US009279006B2

(12) United States Patent
Cohen

(10) Patent No.: US 9,279,006 B2
(45) Date of Patent: Mar. 8, 2016

(54) ANTI-MALARIA VACCINE

(75) Inventor: Joseph D Cohen, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 837 days.

(21) Appl. No.: 11/917,788

(22) PCT Filed: Jun. 29, 2006

(86) PCT No.: PCT/EP2006/006407
§ 371 (c)(1),
(2), (4) Date: May 30, 2008

(87) PCT Pub. No.: WO2007/003384
PCT Pub. Date: Jan. 11, 2007

(65) Prior Publication Data
US 2008/0317787 A1 Dec. 25, 2008

(30) Foreign Application Priority Data
Jun. 30, 2005 (GB) .................................. 0513421.8

(51) Int. Cl.
| A61K 39/00 | (2006.01) |
| A61K 39/002 | (2006.01) |
| A61P 37/02 | (2006.01) |
| C07K 14/445 | (2006.01) |
| A61K 35/68 | (2006.01) |
| A61K 39/015 | (2006.01) |
| A61K 39/29 | (2006.01) |

(52) U.S. Cl.
CPC ............... *C07K 14/445* (2013.01); *A61K 35/68* (2013.01); *A61K 39/015* (2013.01); *A61K 39/292* (2013.01); *A61K 2039/53* (2013.01); *A61K 2039/545* (2013.01); *A61K 2039/55555* (2013.01); *A61K 2039/55572* (2013.01); *A61K 2039/55577* (2013.01); *A61K 2039/6075* (2013.01); *A61K 2039/627* (2013.01); *C07K 2319/00* (2013.01); *C12N 2730/10122* (2013.01)

(58) Field of Classification Search
None
See application file for complete search history.

(56) References Cited

U.S. PATENT DOCUMENTS

| 4,235,877 A | 11/1980 | Fullerton |
| 4,372,945 A | 2/1983 | Likhite |
| 4,474,757 A | 10/1984 | Arnon et al. |
| 4,837,016 A | 6/1989 | Holder et al. |
| 4,912,094 A | 3/1990 | Myers et al. |
| 5,057,540 A | 10/1991 | Kensil et al. |
| 6,083,716 A | 7/2000 | Wilson et al. |
| 2009/0053265 A1* | 2/2009 | Corradin et al. ............ 424/272.1 |
| 2009/0285879 A1* | 11/2009 | Pau et al. ........................ 424/450 |

FOREIGN PATENT DOCUMENTS

| EP | 0468520 | 7/1991 |
| EP | 0549074 | 12/1992 |
| EP | 0689454 | 3/1994 |
| EP | 0362279 | 1/1995 |
| EP | 0761231 | 3/1997 |
| EP | 0761231 A1 * | 3/1997 |
| EP | 1623720 | 2/2006 |
| GB | 2122204 | 5/1983 |
| GB | 2220211 | 5/1983 |
| WO | WO 94 00153 | 1/1990 |
| WO | WO 91/11516 | 8/1991 |
| WO | WO 91/18922 | 12/1991 |
| WO | WO 92/11868 | 7/1992 |
| WO | WO 93/10152 * | 5/1993 |
| WO | WO 94/21292 | 9/1994 |
| WO | WO 95/17209 | 6/1995 |
| WO | WO 95/17210 | 6/1995 |
| WO | WO 90/01496 | 2/1996 |
| WO | WO 96/02555 | 2/1996 |
| WO | WO 96/11711 | 4/1996 |
| WO | WO 96/33739 * | 10/1996 |
| WO | WO 98/05355 | 2/1998 |
| WO | WO 98/15287 | 4/1998 |
| WO | WO 98/16247 | 4/1998 |
| WO | WO 98/43690 | 10/1998 |
| WO | WO 98/56414 | 12/1998 |
| WO | WO 95/12565 | 3/1999 |
| WO | WO 99/10008 | 3/1999 |
| WO | WO 99/11241 | 3/1999 |
| WO | WO 02/077195 | 10/2002 |
| WO | WO 03/046142 | 6/2003 |
| WO | WO 2004/037189 | 5/2004 |
| WO | WO 2004/037189 A2 * | 5/2004 |
| WO | WO 2004/044167 | 5/2004 |
| WO | WO 2006/029887 | 3/2006 |
| WO | WO 2006/040334 | 4/2006 |

OTHER PUBLICATIONS

Stoute et al. New Eng. J. Med. 336: 86-91, 1997.*
Richards et al. Infect. Immun. 66: 2859-2865, 1998.*
Sun et al. J. Immunol. 171: 6961-6967, 2003.*
Stewart et al. Am. J. Trop. Med. Hyg. 63: 3 Suppl, p. 255, #336, 2001.*
McGrath et al. Am. J. Trop. Med. Hyg. 65: 3, pp. 242-243, #303, 2001.*
D.M. Gordon, T.W. McGovern, U. Krzych, J.D. Cohen, Schneider, R. LaChance, D.G. Heppner, G. Yuan, M. Hollingdale, M. Slaoui, P. Hauser, P. Voet, J.C. Sadoff and W.R. Ballou: "Safety, immunogenicity and efficacy of a recombinantly produced Plasmodium falciparum circumsporozoite protein—hepatitis B surface antigen subunit vaccine". J. Infect. Dis. (1995) 171:1576-1585.

(Continued)

*Primary Examiner* — S. Devi
(74) *Attorney, Agent, or Firm* — James T. Olesen

(57) ABSTRACT

There is provided, inter alia, a method for the prophylaxis of productive malaria infection in travelers to endemic regions comprising the administration of suitable amounts of a formulation comprising a *Plasmodium* antigen or an immunogenic fragment or derivative thereof and an adjuvant, comprising a lipid A derivative and a saponin in a liposome formulation.

4 Claims, 6 Drawing Sheets

(56) References Cited

OTHER PUBLICATIONS

J.A. Stoute, M. Slaoui, D.G. Heppner, P. Momin, K.E. Kester, P. Desmons, B.T. Wellde, N. Garçon, U. Krzych, M. Marchand, W.R. Ballou and J.D. Cohen : "A preliminary evaluation of a recombinant circumsporozoite protein vaccine against *Plasmodium falciparum* malaria". The New England Journal of Medicine (1997) 336:86-91.
J.A. Stoute, K.E. Kester, U. Krzych, B.T. Wellde, T. Hall, K. White, G. Glenn, C.F. Ockenhouse, N. Garcon, R. Schwenk, D.E. Lanar, P. Sun, P. Momin, R.A. Wirtz, C. Golenda, M. Slaoui, G. Wortmann, C. Holland, M. Dowler, J. Cohen and W.R. Ballou : "Long-term efficacy and immune responses following immunization with the RTS,S Malaria vaccine". J. Infect. Dis. (1998) 178(4):1139-1144.
A. Lalvani, P. Moris, G. Voss, A.A. Pathan, K.E. Kester, R. Brookes, E. Lee, M. Koutsoukos, M. Plebanski, M. Delchambre, K.L. Flanagan, C. Carton, M. Slaoui, C. Van Hoecke, W.R. Ballou, A.V.S. Hill and J. Cohen : "Potent induction of focused Th1-type cellular and humoral immune responses by RTS,S/SBAS2, a recombinant *Plasmodium falciparum* Malaria vaccine". J. Infect. Dis. (1999) 180:1656-1664.
J.F. Doherty, M. Pinder, N. Tornieporth, C. Carton, L. Vigneron, P. Milligan, W.R. Ballou, C.A. Holland, K.E. Kester, G. Voss, P. Momin, B.M. Greenwood, K.P.W.J. McAdam and J. Cohen : "A phase I safety and immunogenicity trial with the candidate Malaria vaccine RTS,S/SBAS2 in semi-immune adults in The Gambia". Am. J. Trop. Med. Hyg. (1999) 61(6):865-868.
A. Alloueche, H. Silveira, D.J. Conway, K. Bojang, T. Doherty, J. Cohen, M. Pinder and B.M. Greenwood : "High-throughput sequence typing of T-cell epitope polymorphisms in *Plasmodium falciparum* circumsporozoite protein". Molecular and Biochemical Parasitology (2000) 106:273-282.
K.E. Kester, D.A. McKinney, C.F. Ockenhouse, D.G. Heppner, B.T. Wellde, J.A. Stoute, B.T. Hall, U. Krzych, G.E. Poley, A. Montemarano, P.F. Sun, R. Schwenk, K. White, T. Le, C. Golenda, R.A. Gasser, D. Gordon, G. Wortmann, R.S. Miller, G.M. Glenn, J. Palensky, J. Cohen and W.R. Ballou : "Efficacy of recombinant circumsporozoite protein vaccine regimens against experimental *Plasmodium falciparum* malaria. RTS,S Malaria vaccine evaluation group". The Journal of Infectious Diseases (2001) 183:640-647.
K.A. Bojang, P.J.M. Milligan, M. Pinder, L Vigneron, A. Alloueche, K.E. Kester, W.R. Ballou, D.J. Conway, W.H.H. Reece, P. Gothard, L. Yamuah, M. Delchambre, G. Voss, B.M. Greenwood, A. Hill, K.P. W.J. McAdam, N. Tornieporth, J.D. Cohen, T. Doherty: "Efficacy of RTS,S/AS02 malaria vaccine against *Plasmodium falciparum* infection in semi-immune adult men in The Gambia: a randomised trial". The Lancet (2001) 358: 1927-34.
A. Alloueche, P. Milligan, D.J. Conway, M. Pinder, K. Bojang, T. Doherty, N. Tornieporth, J. Cohen, B.M. Greenwood: "Protective efficacy of the RTS,S/AS02 *Plasmodium falciparum* malaria vaccine is not strain specific". American Journal of Tropical & Medicine Hygiene (2003) 68 (1): 97-101.
N. Garcon, D.G. Heppener, J. Cohen: "Development of RTS,S/AS02: a purified subunit-based malaria vaccine candidate formulated with a novel adjuvant". Expert Rev. Vaccines (2003) 2 (2): 231-38.
D.G. Heppner, J.D. Cohen, J.F. Cummings, W.R. Ballou, C.F. Ockenhouse, K.E. Kester: "Adjuvanted RTS,S and other protein-based pre-erythrocytic stage malaria vaccines". In: New Generation Vaccines/3$^{rd}$ edition—revised and expanded—edited by M. Levine, J. Kaper, R. Rappuoli, M. Liu and M. Good (2004).
P. Sun, R. Schwenk; K. White, J. Stoute, J. Cohen, W.R. Ballou, G. Voss, K.E. Kester, D.G. Heppner, U. Krzych: "Protective immunity induced with malaria vaccine, RTS,S, is linked to *Plasmodium falciparum* circumsporozoite protein-specific CD4$^+$ and CD8$^+$ T cells producing IFN-γ". Journal of Immunol Dec. 15, 2003:171 (2): 6961-7.
W.R. Ballou, F. Dubovsky, K.E. Kester, J. Lyon, D.E. Lanar, A. Saul, B.K. Giersing, P. Druihle, D. Carucci, T.L. Richie, G. Corradin, B.F. Hall, A.V.S. Hill, C. Diggs, M. Arevalo-Herrera, J. Cohen: "Update on the clinical development of candidate malaria vaccines". Am. J. Trop. Med Hyg. (2004) 71 (suppl 2): 239-247.
M. Pinder, W.H.H. Reece, M. Plebanski, P. Akinwunmi, K.L. Flanagan, E.A.M. Lee, T. Doherty, P. Milligan, A. Jaye, N. Tornieporth, R. Ballou, K.P.M.J. McAdam, J. Cohen, A.V.S. Hill/ "Cellular immunity induced by the recombinant *Plasmodium falciparum* malaria vaccine, RTS,S/AS02, in semi-immune adults in The Gambia". Clin Exp Immunol 2004; 135:286-293.
Epstein JE, Charoenvit Y, Kester KE, Wang R, Newcomer R, Fitzpatrick S, Richie TL, Tornieporth N, Heppner DG, Ockenhouse C, Majam V, Holland C, Abot E, Ganeshan H, Berzins M, Jones T, Freydberg CN, NG J, Norman J, Carucci DJ, Cohen J, Hoffman SL, "Safety, tolerability, and antibody responses in humans after sequential immunization with a PfCSP DNA vaccine followed by the recombinant protein vaccine RTS,S/AS02A." Vaccine. Apr. 16, 2004;22 (13-14):1592-603.
Reece WH, Pinder M, Gothard PK, Milligan P, Bojang K, Doherty T, Plebanski M, Akinwunmi P, Everaere S, Watkins KR, Voss G, Tornieporth N, Alloueche A, Greenwood BM, Kester KE, McAdam KP, Cohen J, Hill AV. "A CD4(+) T-cell immune response to a conserved epitope in the circumsporozoite protein correlates with protection from natural Plasmodium falciparum infection and disease." Nat Med. Apr. 2004;10 (4):406-10. Epub Mar. 14, 2004.
Wang R, Epstein J, Charoenvit Y, Baraceros F.M., Rahardjo N, Gay T, Banania JG, Chattopadhyay R, De La Vega P; Richie TL, Tornieporth N, Doolan DL, Kester KE, Heppern DG, Norman J, Carucci D, Cohen J, Hoffman S.L. "Induction in Humans of CD8+ and CD4+ T cell and antibody responses by sequential immunization with Malaria DNA and recombinant protein" Journal of Immunol 2004; 172: 5561-5569.
P.L. Alonso, J. Sacarlal, J.J. Aponte, A. Leach, E. Macete, J. Milman, I Mandomando, B. Spiesens, C. Guinovart, M. Espasa, Q. Bassat, P. Aide, O. Ofori-Anyianam, M.M. Navia, S. Corachan, M. Ceuppens, M-C Dubois, M-A. Demoitie, F. Dubovsky, C. Menendez, N. Tornieporth, W.R. Ballou, R. Thompson, J. Cohen: "Efficacy of the RTS,S/AS02A vaccine against *Plasmodium falciparum* infection and disease in young African children: randomized controlled trial". The Lancet (2004) 364, 1411-20.
Douglas S. Walsh, Sathit Pichyangkul, Montip Gettayacamin, Pongsri Tongtawe, Claire-Anne Siegrist, Pranee Hansukjariya, Kent E. Kester, Carolyn A. Holland, Gerald Voss, Joe Cohen, Ann V. Stewart; R. Scott Miller, W. Ripley Ballou, D. Gray Heppner: Safety and immunogenicity of RTS,S+Trap malaria vaccine, formulated in the AS02A adjuvant system, in infant rhesus monkeys. Am. J. Trop. Med. Hyg. (2004) 70 (5), 499-509.
G. Heppner, K. Kester , C. Ockenhouse, N. Tornieporth, O. Ofori , J. Lyon, A. Stewart, P. Dubois, D. Lanar, U. Krzych, P. Moris, E. Angov, J. F. Cummings, A. Leach, T. Hall, S. Dutta, R. Schwenk, C. Hillier, A. Barbosa, L. Ware, L. Nair, C. Darko, M.. Withers, B. Ogutu, M. Polhemus, M. Fukuda, S. Pichyangkul, M. Gettyacamin, C. Diggs, L. Soisson, J. Milman, M-C. Dubois, N. Garcon, K. Tucker, J. Wittes, C. Plowe, M. Thera, O. Duombo, M. Pau, J. Goudsmit, R. Ballou, J. Cohen: "Towards an RTS,S-based, multi-stage, multi-antigen vaccine against falciparum malaria: progress at the Walter Reed Army Institute of Research". Vaccine (2005) 23, 2243-50.
Bojang K. A., Olodude, F., Pinder, M., Ofori-Anyinam, O., Vigneron, L., Fitzpatrick, S., Njie, F., Kassanga, A., Leach, A., Milman, J., Rabinovich, R., McAdam, K. P., Kester, K. E., Heppner, D. G., Cohen, J. D., Tornieporth, N., and Milligan, P. J.: "Safety and Immunogenicity of RTS,S/AS02A Candidate Malaria Vaccine in Gambian Children". Vaccine (2005) 23 (32), 4148-4157.
Pedro L Alonso, Jahit Sacarlal, John J Aponte, Amanda Leach, Eusebio Macete, Pedro Aide, Betuel Sigauque, Jessica Milman, Inacio Mandomando, Quique Bassat, Caterina Guinovart, Mateu Espasa, Sabine Corachan, Marc Lievens, Margarita M Navia, Marie-Claude Dubois, Clara Menendez, Filip Dubovsky, Joe Cohen, Ricardo Thompson, W Ripley Ballou: "Duration of protection with RTS,S/AS02A malaria vaccine in prevention of Plasmodium falciparum disease in Mozambican children: single-blind extended follow-up of a randomized controlled trial". The Lancet (2005) 366, 2012-18.
Susanna J. Dunachie, Michael Walther, Jenni M. Vuola , Daniel P. Webster, Sheila M. Keating, Tamara Berthoud, Laura Andrews, Philip Bejon, Ian Poulton, Geoffrey Butcher, Katherine Watkins, Robert E. Sinden, Amanda Leach, Philippe Moris, Nadia

(56) References Cited

OTHER PUBLICATIONS

Tornieporth, Joerg Schneider, Filip Dubovsky, Eveline Tierney, Jack Williams, D. Gray Heppner, Jr, Sarah C. Gilbert, Joe Cohen, Adrian V.S. Hill: "A clinical trial of prime-boost immunisation with the candidate malaria vaccines RTS,S/AS02A and MVA-CS". Vaccines (2006) 24 (15), 2850-59.
JoséA. Stoute, D. Gray Heppner, Carl J. Mason, Joram Siangla, Malachi O. Opollo, Kent E. Kester, Laurence Vigneron, Gerald Voss, Michael J. Walter, Nadia Tornieporth, Joe D. Cohen, W. Ripley Ballou: "Phase 1 safety and immunogenicity trial of malaria vaccine RTS,S/AS02A in adults in a hyperendemic region of western Kenya". Am. J. Trop. Med. Hyg. (2006) 75 (1), 166-170.
Walsh DS, Gettayacamin M; Leitner WW, Lyon JA, Stewart VA, Marit G, Pichyangkul S, Gosi P, Tongtawe P; Kester KE, Holland CA, Kolodny N, Cohen J, Voss G, Ballou WR, Heppner DG: "Heterologous prime-boost immunization in rhesus macaques by two, optimally spacedparticle-mediated epidermal deliveries of Plasmodium falciparum circumsporozoite protein-encoding DNA, followed by intramuscular RTS,S/AS02A" Vaccine (2006) 24 (19), 4167-78.
Sonia Enosse, Carlota Dobano, Diana Quelhas, John J. Aponte, Marc Lievens, Amanda Leach, Jahit Sacarlal, Brian Greenwood, Jessica Milman, Filip Dubovsky, Joe Cohen, Ricardo Thompson, W. Ripley Ballou, Pedro L. Alonso, David J. Conway, Colin J. Sutherland: "RTS,S/AS02A Malaria Vaccine does not induce parasite CSP T Cell epitope selection and reduces multiplicity of infection". Plos Clinical Trials (May 2006) (e5), 001-0010.
Ann Stewart, Douglas Walsh, Shannon McGrath, Kent Kester, James Cummings, Gerald Voss, Martine Delchambre, Nathalie Garcon, Joe Cohen, Gray Heppner: "Cutaneous delayed-type hypersensitivity (DTH) in a multi-formulation comparator trial of the anti-falciparum malaria vaccine candidate RTS,S in rhesus macaques". Vaccine (2006) 24 (42-43),6493-6502.
Ann Stewart, Shannon McGrath, Douglas Walsh, Stacey Davis, Aaron Hess, Lisa Ware, Kent Kester, James Cummings, Robert Burge, Gerald Voss, Martine Delchambre, Nathalie Garcon, Douglas Tang, Joe Cohen, Gray Heppner: "Pre-clinical evaluation of new adjuvant formulation to improve the immunogenicity of the malaria vaccine RTS,S/AS02A". Vaccine (2006) 24 (42-43), 6483-92.
Ann Stewart, Shannon McGrath, Patrice Dubois, Maria Pau, Pascal Mettens, Joseph Shott, Michelle Cobb, Robert Burge, David Larson, Lisa Ware, Marie-Ange Demoitie, Gerrit Weverling, Babak Bayat, Jerome Custers, Marie-Claude Dubois, Joe Cohen, Jaap Goudsmit, Gray Heppner: "Priming with an Adenovirus 35-Circumsporozoite Protein (CS) vaccine followed by RTS,S/AS01B Boosting Significantly Improves Immunogenicity to Plasmodium falciparum CS compared to that with either Malaria vaccine alone". Infection & Immunity (2007) 75 (5), 2283-2290.
E. Macete, J.J. Aponte, C. Guinovart, H. Sacarlal, O. Ofori-Anyinam, I. Mandomando, M. Espasa, C. Bevilacqua, A. Leach, MC. Dubois, D.G. Heppner, L. Tello, J. Milman, J. Cohen, F. Dubovsky, N. Tornieporth, R. Thompson, P. Alonso: "Safety and Immunogenicity of the RTS,S/AS02A candidate malaria vaccine in children aged 1-4 in Mozambique". Tropical Medicine & International Health (2007) 12 (1), 37-46.
Ken Kester, Denise McKinney, Nadia Tornieporth, Christian Ockenhouse, Gray Heppner, Ted Hall, Bruce Wellde, Kate White, Peifang Sun, Robert Schwenk, Urszula Krzych, Martine Delchambre, Gerald Voss, Marie-Claude Dubois, Robert Grasser, Megan Dowler, Megan O'Brien, Janet Wittes, Robert Wirtz, Joe Cohen, Ripley Ballou: "A phase I/IIa safety, immunogenicity, and efficacy bridging randomized study of a two-dose regimen of liquid and lyophilized formulations of the candidate malaria vaccine RTS,S/AS02A in malaria-naïve adults". Vaccine (2007) 25 (29), 5359-5366.
Eusebio Macete, Jahit Sacarlal, John Aponte, Amanda Leach, Margarita Navia, Jessica Milman, Caterina Guinovart, Inacio Mandomando, Yolanda Lopez-Pua, Marc Lievens, Alex Owusu, Marie-Claude Dubois, Conor Cahill, Marguerite Koutsoukos, Marla Sillman, Ricardo Thompson, Filip Dubovsky, Ripley Ballou, Joe Cohen, Pedro Alonso: "Evaluation of two formulations of adjuvanted RTS,S malaria vaccine in children aged 3 to 5 years living in a malaria-endemic region of Mozambique: a Phase I/IIb randomized double-blind bridging trial". Trials (2007) 8, 11.
John Aponte, Pedro Aide, Montse Renom, Inacio Mandomando, Quique Bassat, Jahit Sacarlal, Nelia Manaca, Sarah Lafuente, Arnoldo Babosa, Amanda Leach, Marc Lievens, Johan Vekemans, Betuel Sigauque, Marie-Claude Dubois, Marie-Ange Demoitie, Marla Sillman, Barbara Savarese, John McNeil, Eusebio Macete, Ripley Ballou, Joe Cohen, Pedro Alonso: "Safety of the RTS,S/AS02D candidate malaria vaccine in infants living in a highly endemic area of Mozambique: a double blind randomized controlled phase I/IIb trial". Lancet (2007) 370, 1543-1551.
Jahit Sacarlal, John Aponte, Pedro Aide, Inacio Mandomando, Quique Bassat, Caterina Guinovart, Amanda Leach, Jessica Milman, Eusebio Macete, Mateu Espasa, Opokua Ofori-Anyinam, Joelle Thonnard, Filip Dubovsky, Ripley Ballou, Joe Cohen, Pedro Alonso: "Safety of the RTS,S/AS02A malaria vaccine in Mozambican children during a phase IIb trial". Vaccine (2008) 26, 174-184.
Kent Kester, James Cummings, Christian Ockenhouse, Robin Nielsen, Ted Hall, Daniel Gordon, Robert Schwenk, Urszula Krzych, Carolyn Holland, Gregory Richmond, Megan Dowler, Jackie Williams, Robert Wirtz, Nadia Tornieporth, Laurence Vigneron, Martine Delchambre, Marie-Ange Demoitie, Ripley Ballou, Joe Cohen, Gray Heppner: "Phase 2a trial of 0, 1 and 3 month and 0, 7 and 28 day immunization schedules of malaria vaccine RTS,S/AS02 in malaria-naïve adults at the Walter Reed Army Institute of Research". Vaccines (2008) 26, 2191-2202.
Mettens Pascal, Dubois Patrice, Demoitie Marie-Ange, Bayat Babak, Donner Marie-Noëlle, Bourguignon Patricia, Stewart Ann, Heppner Gray, Garcon Nathalie, Cohen Joe: "Improved T cell responses to Plasmodium Falciparum circumsporozoite protein in mice and monkeys induced by a novel formulation of RTS,S vaccine antigen". Vaccine (2008) 26, 1072-1082.
Bejon P, Lusingu J, Olotu A, Leach A, Lievens M, Vekemans J, Mshamu S, Lang T, Gould J, Dubois MC, Demoite MA, Stallaert JF, Vansadia P, Carter T, Njuguna P, Awuondo K, Malabeja A, Abdul O, Gesase S, Mturi N, Drakeley C, Savarese B, Villafana T, Ballou R, Cohen J, Riley E, Lemnge M, Marsh K, Von Seidlein L: "Efficacy of RTS,S/AS01E Vaccine against Malaria in Children 5 to 17 months of age". NEJM (2008), 359, 24: 2521-32.
Adbulla S, Oberholzer R; Juma O, Kubhoja S, Machera F, Membi C, Omari S, Urassa A, Mshinda H, Jumanne A, Salim N, Shomari M, Aebi T, Schellenberg D, Carter T, Villafana T, Demoitie MA, Dubois MC, Leach A, Lievens M, Vekemans J, Cohen J, Ballou R, Tanner M: Safety and Immunogenicity of RTS,S/AS02D Malaria Vaccine in Infants. NEJM (2008) 359, 24: 2533-44.
Pichyangkul S, Kum-Arb U, Yongvanitchit K, Limsalakpetch A, Gettayacamin M, Lanar D E, Ware L A, Stewart V A, Heppner D G, Mettens P, Cohen J D, Ballou W R, Fukuda M M: "Preclinical evaluation of the safety and immunogenicity of a vaccine consisting of Plasmodium falciparum liver-stage antigen 1 with adjuvant AS01B administered alone or concurrently with the RTS,S/AS01B vaccine in rhesus primates". Infection and immunity 2008;76(1):229-38.
Bojang K, Milligan P, Pinder M, Doherty T, Leach A, Ofori-Anyinam O, Lievens M, Kester K, Schaecher K, Ballou R, Cohen J.: "Five year safety and immunogenicity of GlaxoSmithKline's candidate malaria vaccine RTS,S/AS02 following administration to semi-immune adult men living in a malaria-endemic region of The Gambia". Hum Vaccines (2009) 5 (4), 1-6.
Guinovart C; Aponte J; Sacarlal J; Aide P; Leach A; Bassat Q; Macete E; Dobano C; Lievens M; Loucq C; Ballou R; Cohen J: Alonso P.: "Insights into long-lasting protection induced by RTS,S/AS02A malaria vaccine: further results from a phase IIb trial in Mozambican children". PLoSONE (2009) 4 (4): e5165.
Kester K; Cummings J, Ofori-Anyinam O, Ockenhouse C; Krzych U, Moris P, Schwenk R; Nielsen R; Debebe Z, Pinelis E, Juompan L, Williams J, Dowler M, Stewart A, Wirtz R; Dubois MC, Lievens M, Cohen J; Ballou R; Heppner D and the RTS,S Vaccine Evaluation Group: "Randomized, double-blind, phase 2a Trial of falciparum

(56) References Cited

OTHER PUBLICATIONS malaria vaccines RTS,S/AS01B and RTS,S/AS02A in malaria-naive adults: safety, efficacy and immunologic associates of protection". JID (2009) 200: 337-346.
Sacarlal J, Aide P, Aponte J; Renom M; Leach A, Mandomando I, Lievens M, Bassat Q, Lafuente S, Macete E, Vekemans J, Guinovart C, Sigauque B, Sillman M, Milman J, Dubois MC, Demoitie MA, Thonnard J, Menendez C, Ballou R, Cohen J, Alonso P: "Long-term safety and efficacy of the RTS,S/AS02A malaria vaccine in Mozambican children". JID (2009) 200: 329-336.
Polhemus M; Remich S; Ogutu B; Waitumbi J; Otieno L; Apollo S; Cummings J; Kester K; Ockenhouse C; Stewart A; Ofori-Anyinam O; Ramboer I; Cahill C; Lievens M, Dubois MC; Demoitie MA; Leach A; Cohen J; Ballou R; Heppner G. "Evaluation of RTS,S/ AS02A and RTS,S/AS01 B in Adults in a High Malaria Transmission Area". 2009, PLoS 4 (7) e6465.
Owusu-Agyei S, Ansong D, Asante K, Kwarteng Owusu S, Owusu R, Ayiwa Wireko Brobby N, Dosoo D, Osei Akoto A, Osei-Kwakye K, Asafo Adjei E, Owusu Boahen K, Sylverken J, Adjei G, Sambian D, Apanga S, Kayan K, Vekemans J, Ofori-Anyinam O, Leach A, Lievens M, Demoitie MA, Dubois MC, Cohen J, Ballou WR, Savarese B, Chandramohan D, Owusu Gyapong J, Milligan, P Antwi S, Agbenyega T, Greenwood B, Evans J: "Randomized Controlled Trial of RTS,S/AS02D and RTS,S/AS01E Malaria Candidate Vaccines Given According to Different Schedules in Ghanaian Children". 2009, PLoS 4 (10) e7302.
Cohen J: "Malaria vaccine Development: trials, tribulations and reasons for hope". 2009 Human vaccines 5-1 (2-5).
Lell B, Gnandji A, Von Glasenapp I, Haertle S, Oyakhiromen S, Issifou S, Vekemans J, Leach A, Lievens M, Dubois MC, Demoitie MA, Carter T, Villafana T, Ballou W, Cohen J, Kremsner P: "A Randomized Trial Assessing the Safety and Immunogenicity of AS01 and AS02 Adjuvanted RTS,S Malaria Vaccine Candidates in Children in Gabon"; 2009, PLoS 4 (10) e7611.
Waitumbi J, Anyona S, Hunja C, Kifude C, Polhemus M, Walsh D, Ockenhouse C; Heppner G, Leach A; Lievens M, Ballou R, Cohen J, Sutherland C: "Impact of RTS,S/AS02$_A$ and RTS,S/AS01$_B$ on Genotypes of *P. falciparum* in Adults Participating in a Malaria Vaccine Clinical Trial". 2009, PLoS 4 (11)e7849.
Vekemans J, Leach A, Cohen J: "Development of the RTS,S/AS malaria candidate vaccine", 2009 Vaccine 27S: G67-71.
Pichyangkul S, Tongtawe P., Kum-Arb U, Yongvanitchit K, Gettayacamin M; Hollingdale MR, Limsalakpetch A; Stewart A, Lanar D, Dutta S, Angov E; Ware LA, Bergmann-Leitner E; House B; Voss G; Dubois MC, Cohen J, Fukuda M, Heppener D. Miller R.: "Evaluation of the safety and immunogenicity of *Plasmodium falciparum* apical membrane antigen 1, merozoite surface protein 1 or RTS,S vaccines with adjuvant system AS02A administered alone or concurrently in rhesus monkeys". 2009 Vaccine 28: 452-462.
Cohen J, Nussenzweig V, Nussenzweig R, Vekemans J, Leach A.: "From the circumsporozoite protein to the RTS,S/AS candidate vaccine", 2010 Human Vaccines 6 (1): 1-7.
Vahey M., Wang Z, Kester K, Cummings J; Heppner G: Nau M; Ofori-Anyinam O: Cohen J; Coche T; Ballou R; Ockenhouse C.: "Expression of Genes Associated with Immunoproteasome Processing of Major Histocompatibility Complex Peptides Is Indicative of Protection with Adjuvanted RTS,S Malaria Vaccine". 2010 JID 201: 580-589.
Agnandji ST, Asante KP, Lyimo J, Vekemans J, Soulanoudjingar SS, Owusu R, Shomari M, Leach A, Fernandes J, Dosoo D, Chikawe M, Issifou S, Osei-Kwakye K, Lievens M, Paricek M, Apanga S, Mwangoka M, Okissi B, Kwara E, Minja M, Lange J, Boahen O, Kayan K, Adjei G, Chandramohan D, Jongert E, Demoitié MA, Dubois MC, Carter T, Vansadia P, Villafana T, Sillman M, Savarese B, Lapierre D, Ballou WR, Greenwood B, Tanner M, Cohen J, Kremsner PG, Lell B, Owusu-Agyei S, Abdulla S. : "Evaluation of the safety and immunogenicity of the RTS,S/AS01E malaria candidate vaccine when integrated in the expanded program of immunization". 2010 J Infect Dis 202(7): 1076-87.

Aide P, Aponte J, Renom M, Nhampossa T, Sacarlal J, Mandomando I, Bassat Q, Manaca MN, Leach A, Lievens M, Vekemans J. Dubois MC, Loucq C, Ballou R, Cohen J, Alonso P: "Safety, immunogenicity and direction of protection of the RTS,S/AS02$_D$ Malaria vaccine: one year follow-up of a randomized controlled phase I/IIb Trial". 2010 PLoS One 5 (11): e13838.
Cohen J, Benns S, Vekemans J, Leach A: "Le candidat vaccine antipaludique RTS,S/AS est entré en essais cliniques de phase III". 2010 Annales Pharmaceutiques Françaises 68 : 370-9.
J. Lusingu, A. Olotu, A. Leach, M. Lievens, J. Vekemans, A. Olivier, S. Beens, R. Olomi, S. Msham, T. Lang, J. Gould, K. Hallez, Y. Guerra, P. Njuguna, K. Awuondo, A. Malabeja, O. Abdul S. Gesase, D. Dekker, L. Malle, S. Ismael, N. Mturi; C. Drakeley, B. Savarese, T. Villafana, R. Ballou, J. Cohen, E. Riley, M. Lemnge, K. Marsh, P. Bejon, L. Von Seidling: "Safety on the Malaria Vaccine Candidate, RTS,S/AS01E in 5 to17 month old Kenyan and Tanzanian children". 2010 PLoS One 5 (11): e14090.
A. Olotu, A Leach, M. Lievens, J. Vekemans, S. Msham, T. Lang, J Gould, MC Dubois, E. Jongert, P. Vansadia, T. Carter, P. Njuguna, K. Awuondo, A. Malabeja, O. Abdul, S Gesase, N Mturi, C. Drakeley B. Savarese, T. Villafana, D Lapierre, R Ballou, J Cohen, M. Lemnge, N Peshu, K Marsh, E. Riley, L. Seidlei, P. Bejon: "Efficacy of RTS,S/ AS01E malaria vaccine and exploratory analysis on anti-circumsporozoite antibody titres and protection in children aged 5-17 months in Kenya and Tanzania: a randomised controlled trial". 2011 Lancet Infect Dis 11: 102-109.
P. Aide, C. Dobano, J. Sacarlal, J Aponte, I. Mandomando, C. Guinovart, Q. Bassat, M. Renom, L. Puyol, E. Macete, E. Herreros, A. Leach, MC. Dubois, MA. Demoitie, M. Lievens, J. Vekemans, C. Loucq, R. Ballou, J. Cohen, P. Alonso : << Four year immunogenicity of the RTS,S/AS02$_A$ malaria vaccine in Mozambican children during a phase IIb trial. 2011 Vaccine 29 (35): 6059-6067.
P. Bejon, J Cook, E. Bergmann-Leitner, A. Olotu, J. Lusingu, J Mwacharo, J Vekemans, P Njuguna, A. Leach, M Lievens, S Dutta, L Von Seidlein, B Savarese, T Villafana, MM Lemnge, J Cohen, K Marsh, PH. Corran, E Angov, E Riley, and C. Drakeley: "Effect of the Pre-erythrocytic Candidate Malaria Vaccine RTS,S/AS01E on Blood Stage Immunity in Young Children". 2011 JID (204): 9-18.
S. Agnandji, R. Fendel, M. Mestre, M Janssens, J. Vekemans, J. Held, F Gnansounou, S. Haertle, I Von Glasenapp, S. Ayakhirome, L. Mewono, P. Moris, M. Lievens, MA Demoitie, P. Dubois, T. Villafana, E. Jongert, A. Olivier, J. Cohen, M. Esen, P. Kremsner, B. Lell, B. Mordmuller: "Induction of *Plasmodium falciparum*-Specific CD4$^+$ T cells and memory B cells in Gabonese children vaccinated with RTS,S/AS01$_E$ and RTS,S/AS02$_D$". 2011 PLoSOne 6 (4) e18559.
D. Ansong, K. Asante, J. Vekemans, S. Owusu, R. Owusu, N. Brobby, D. Dosoo, A. Osei-Akoto, K. Osei-Kwakye, E. Asafo-Adjei, K. Boahen, J. Sylverken, G. Adjei, D. Sambian, S. Apanga, K. Kayan, M. Janssens, M. Lievens, A. Olivier, E. Jongert, P. Dubois, B. Savarese, J. Cohen, S. Antwi, B. Greenwood, J. Evans, T. Agbenyega, P. Moris, S. Owusu-Agyei "T Cell responses to the RTS,S/AS01$_E$ and RTS,S/AS02$_D$ malaria candidate vaccines administered according to different schedules to Ghanaian children". 2011 PLoSOne 6 (4) e18891.
KP. Asante, S. Abdulla, S. Agnandji, J Lyimo, J. Vekemans, S. Soulanoudjingar, R. Owusu, M. Shomari, A. Leach, E. Jongert, N. Salim, J. Fernandes, D. Dosoo, M. Chikawe, S. Issifou, K. Osei-Kwakye, M. Lievens, M. Paricek, T. Moller, S. Apanga, G. Mwangoka, MC. Dubois, T. Madi, E. Kwara, R. Minja, A. Hounkpatin, O. Boahen, K. Kayan, G. Adjei, D. Chandramohan, T. Carter, P. Vansadia, M. Sillman, B. Savarese, C. Loucq, D. Lapierre, B. Greenwood, J. Cohen, P. Kremsner, S. Owusu-Agyei, M. Tanner, B. Lell: "Safety and efficacy of the RTS,S/AS01$_E$ candidate malaria vaccine given with expanded-programme-on-immunisation vaccines: 19 month follow-up of a randomised, open-label, phase 2 trial". 2011 Lancet Inf Dis 11: 741-49.
Cohen J, Beens S, Veekemans J, Leach A, Schuerman L.: "Development of the RTS,S/AS vaccine candidate from concept to Phase III". 2011 Progress in Parasitology—Parasitology Research Monographs 2: 121-133.
Lumsden J, Schwenk R, Rein L, Moris P, Janssens M, Ofori-Anyinam O, Cohen J, Kester K, Heppner G, Krzych U: "Protective

(56) References Cited

OTHER PUBLICATIONS

Immunity induced with the RTS,S/AS vaccine is associated with IL-2 and TNF-α producing effector and central memory CD4+ T cells". 2011 PLoS One: 6 (7): e20775.
Olotu A, Moris P, Mwacharo J, Vekemans J; Kimani D, Janssens M, Kai O, Jongert E, Lievens M, Leach A, Villafana T, Savarese B, Marsh K, Cohen J, Bejon P: "Circumsporozoite-Specific T Cell Responses in Children Vaccinated with RTS,S/AS01$_E$ and Protection against P. falciparum Clinical Malaria". 2011 PLoS One 6 (10): e25786.
The RTS,S Clinical Trial Partnership: "First results of Phase 3 Trial of RTS,S/AS01 Malaria Vaccine in African Children". 2011 NEJM 365 (20): 1863-75.
Horowitz A, Hafalla JCR, King E, Lusingu J, Dekker D, Leach A, Moris P. , Cohen J, Vekemans J, Villafana T, Corran P, Bejon P, Drakeley C, Von Seidlein L, Riley E: "Antigen-Specific IL-2 Secretion Correlates with NK Cell Responses after Immunization of Tanzanian Children with the RTS,S/AS01 Malaria Vaccine". 2012 J Immunol 188: 5054-62.
The RTS,S Clinical Trials Partnership: "A Phase 3 Trial of RTS,S/AS01 Malaria Vaccine in African Infants". N Engl J Med 2012. Doi: 10.1056/NEJMoa1208394.
Abdulla S, Salim N, Machera F, Kamata R, Juma O, Shomari M, Kubhoja S, Mohammed A, Mwangoka G, Aebi T, Mshinda H, Schellenberg D, Carter T, Villafana T, Dubois MC, Leach A, Lievens M, Vekemans J, Cohen J, Ballou R, Marcel Tanner M: "Randomized, controlled trial of the long term safety, immunogenicity and efficacy of RTS,S/AS02D malaria vaccine in infants living in a malaria-endemic region": Malar J . 2013; 12 (1): 11.
Agnandji, "Final Results of Phase 3 Trial of RTS, S/AS01 Malaria Vaccine in African Children", The New England Journal of Medicine, Massachusetts Medical Society, 365(20):1863-1875 (2011).
Agnandji. "A Phase 3 Trial of RTS,S/AS01 Malaria Vaccine in African Infants" N Engl J Med 2012, DOI:10.1056/NEJMoa1208934.
Aidoo et al, 232 "Cytotoxic T-lymphocyte epitopes for HLA-B53 and other HLA types in the malaria vaccine candidate live-stage antigen 3", Infection and Immunity. 2000 American Society for Microbiology, 68(1):227-232.
Alonso, et al., Population and health in developing countries, vol. 1, Population, health and survival at INDEPTH sites. Ottawa: International development research center (IDRC), 2001, Chapter 15, p. 189-195.
Brazolot-Millan, et al., "CpG DNA can induce strong Th1 humoral and cell-mediated immune responses against hepatitis B surface antigen in young mice", PNAS, 1998 The National Academy of Sciences, 95(26):15553-15558.
Breman, et al., "The intolerable burden of malaria: what's new, what's needed", Am J Trop Med Hyg., 2004 71(2_suppl):0-i-.
Caspers, et al., "The circumsporozoite protein gene from NF54, a Plasmodium falciparum isolate used in malaria vaccine trials", Molecular and Biochemical Parasitology, 1989 Elsevier Science Publishers B.V., 35:185-190.
Charoenvit, et al, "CD4+ T cell and gamma interferon-dependant protection against murine malaria by immunization with linear synthetic peptides from a Plasmodium Yoelii 17 Kilodalton hepatocyte erythrocyte protein", Infection and Immunity, 1999 American Society for Microbiology, 67(11):5604-5614.
Chulay et al, (1986) *Malaria transmitted to humans by mosquitoes infected from cultured Plasmodium falciparum.* Am J Trop Med Hyg. Jan:35(1):66-8.
Dame, et al., "Structure of the gene encoding the immunodominant surface antigen on the sporozoite of the human malaria parasite Plasmodium falciparum", Science, 1984 ;225:593-9 (abstract).
Daubersies, et al., "Protection against Plasmodium falciparum malaria in chimpanzees by immunization with the conserved pre-erythrocytic liver stage antigen 3", Nature Medicine vol. 6 No. 11 Nov. 2000 p. 1258-1263.
Davis, et al., "CpG DNA is a potent enhancer of specific immunity in mice I munized with recombinant hepatitis B surface antigen", J. Immunol., 1998 The American Association of Immunologists, 160(2):870-876.

Hay, et al., "The global distribution and population at risk of malaria: past, present, and future", The Lancet Infectious Diseases, 2004 http://infectionthelancet.com; 4(6):327-336.
Heppner, et al, "Towards an RTX,S-based, multistage, multi-antigen vaccine against falciparum malaria: progress at the Walter Reed Army Institute of Research", Vaccine, 2005 Elsevier Ltd, 23:2243-2250.
Herrington, et al, "Safety and immunogenicity in man of a synthetic peptide malaria vaccine against Plasmodium falciparum sporozoites" Nature, 1987 Nature Publishing Group, 328:257, 1987.
Hilgers et al. (1986). *Synergistic effects of synthetic adjuvants on the humoral immune response.* Int. Arch. Allergy.Immunol., 79(4):392-6.
Hilgers et al. (1987). *Synthetic sulpholipopolysaccharides: novel adjuvants for humoral immune responses.* Immunology, 60(1):141-6.
Hoffman SL (1996) "Malaria Vaccine Development: a multi-immune response approach" Am Soc Microbiol Press Ed Hoffman SL, Chapter 3 "Attacking the infected hepatocyte".
Kensil, "Separation and characterization of saponins with adjuvant activity from Quillaja saponaria Molina cortex", J. Immunology, 1991 The American Association of Immunologists, 146:431-437.
Kensil C. R. (1996) *Saponins as vaccine adjuvants.* Crit Rev Ther Drug Carrier Syst 12 (1-2):1-55.
Klausner, et al., "An attack on all fronts", Nature, 2004 Nature Publishing Group;430:930-931.
Krieg, et al., "CpG motifs in bacterial DNA trigger direct B-cell activation", Nature, 1995 Nature Publishing Group, 374:546-549.
Kurtis et al., "Pre-erythrocytic immunity to Plasmodium falciparum the case for an LSA-1 vaccine", Trends in Parasitology vol. 17 No. 5 May 2001 p. 219-223.
Lacaille-Dubois, et al., "A review of the biological and pharmacological activities of saponins", Phytomedicine, 1996 Gustav Fischer Verlag, 12:363-386.
Loscertales, et al., "Epidemiology and clinical presentation of respiratory syncytial virus infection in a rural area of southern Mozambique", Pediatr Infect Dis J., 2002 Lippincott Williams & Wilkins, Inc., 21:148-155.
McCluskie, et al., "Cutting edge: CpG is a potent enhancer of systemic and mucosal immune responses against hepatitis B surface antigen with intranasal administration to mice", J. Immunol., 1998 The American Association of Immunologists, 161(9):4463-4466.
Meraldi et al., "Natural antibody response to Plasmodium falciparum Exp-1, MSP-3 and GLURP long synthetic peptides and associated with protection", Parasite Immunology, 2004 Blackwell Publishing, 26, 265-272.
Mossmann, et al., TH1 and TH2 cells: different patterns of lymphokine secretion lead to different functional properties, Annual Review of Immunology, 7:145-173, 1989 Annual Reviews Inc.
Musti, et al., "Transcriptional mapping of two yeast genes coding for glyceraldehydes 3-phosphate dehydrogenase isolated by sequence homology with the chicken gene", Gene, 1983Elsevier, 25:133-143.
Polley, et al., "Human antibodies to recombinant protein constructs of Plasmodium falciparum apical membrane antigen 1 (AMA1) and their associations with protection from malaria", Vaccine 23, 2004 Elsevier Ltd., 718-728.
Powell and Newman (Editors) (1995) *Vaccine Design—the subunit and adjuvant approach*, Pharmaceutical Biotechnology, vol. 61, Plenum Press New York.
Ribi et al, (1986) *Modulation of humoral and cell-mediated immune responses by a structurally established nontoxic lipid A.* Immunobiology and Immunopharmacology of bacterial endotoxins. Plenum Publ. Corp., NY, p. 407-420.
Richards, "Liposomes containing, Lipid A serve as an adjuvant for induction of antibody and cytotoxic T-Cell responses against RTS,S malaria antigen", Infection and Immunity, 1998 The American Society for Microbiology, 66(6):2859-2865.
Saute, et al., "Malaria in southern Mozambique: Malariometric indicators and malaria case definition in Manhica district", Trans R Soc Trop Med Hyg Nov.-Dec. 2003; 97(6):661-666.
Stowers et al., "Vaccination of monkeys with recombinant Plasmodium falciparum apical membrane antigen 1 confers protection against blood-stage malaria", Infection and Immunity, Dec. 2002 p. 6961-6967.

(56) References Cited

OTHER PUBLICATIONS

Valenzuela P, Gray P, Quiroga M, Zaldivar J, Goodman H, Rutter W. (1979) *Nucleotide sequence of the gene coding for the major protein of hepatitis B virus surface antigen*. Nature 260, 815-819.
Valenzuela, et al., "Nucleotide sequence of the gene coding for the major protein of hepatitis B virus surface antigen", Nature, 1979 Nature Publishing Group, 280:815-819, (abstract).
World Health Organization. Management of severe malaria, a practical handbook. Second edition, 2000. http://mosquito.who.int/docs/hbsm.pdf.
Young, et al., "Expression of Plasmodium falciparum circumsporozoite proteins in *Escherichia coli* for potential use in a human malaria vaccine" Science 1985; 228:958-62 (abstract).
Stewart, V A; McGrath, S M I; Davis, S A; Manganello, L M; Kester, K E; Cohen, J; Voss, G; Heppner, D G., "Comparison of Three Novel Adjuvants and an Accelerated Administration Schedule in Rhesus Macaques for Optimizing of the RTS, S Anti-Falciparum Malaria Vaccine Candidate", abstract, The American journal of tropical medicine and hygiene, 65:232. Nov. 13, 2001.
Holland, CA; Williams, J; Heppner, DG; Tornieporth, N; Vigneron, L; Delchambre, M; Cohen, J; Kester, KE, "Humoral immune responses in recipients of RTS,S/AS02 when given in two short course schedules", abstract.The American journal of tropical medicine and hygiene, 65:232. Nov. 13, 2001.
McGrath, SM; Davis, S A; Manganello, I M; Kester, K E; Voss, G; Cohen, J; Heppner, D G; Stewart, V A, "Use of the Elispot Assay in Rhesus Macaques for Optimizing of the RTS, S Malaria Vaccine Candidate With New Adjuvant Formations", abstract, American Society of Tropical Medicine and Hygiene, 65:242. Nov. 13, 2001.
Holland CA Williams J, Heppner DG, Tornieporth N, Vigneron L Delchambre M, Wirtz RA, Cohen J, Kester KE "Humoral immune responses in recipients of rts,s/as02 when given in two short course schedules" poster Nov. 13, 2001.
Kester, Kent E, "Safety, Immunogenicity, and Preliminary Efficacy of Two Short Courses Schedules of RTS/As02" Nov. 13, 2001.
V. Ann Stewart, "Optimization of the anti-falciparum malaria vaccine candidate RTS, S in the rhesus macaque" presentation (associated with 1c above). Nov. 13, 2001.
Dubois, P.; Stewart, A. ,"Induction of antigen specific CD4 and CD8 T cell responses after vaccination with proteins combined to adjuvants" Jun. 23-25, 2003.
Folasade Olodude & Eusebio Macete, MRC, Gambia & CSIM, Mozambique, "Preliminary assessment of the safety and immunogenicity of the RTS,S/AS02A malaria vaccine candidate in 1-11 year old children". Jun. 23-25, 2003.
Meeting agenda Jun. 23-25, 2003.
Wootton, D; Opera, H; Dube-mbeye, Q; Kanjala, M; Neate, C; Kirby, P; Milligan, P; Molyneux, M; Dunyo, S; Winstanley, P, "A dose-ranging, phase II trial of chlorproguanil-dapsone with 3 doses of artesunate for the treatment of acute uncomplicated P. falciparum malaria" Nov. 13-18, 2005.
Sah, S; South, R; Ali, R; Kebede, F, "Behaviour change for improved malaria prevention and treatment in White Nile State (WNS), Sudan". Nov. 13-18, 2005.
Bruegge, E; Dunford, C; Gray, B; Davis, R; South, R; Armarklemesu, M; Dearden, K, "Microfinance Against Malaria". Nov. 13-18, 2005.
South, Richard, "Partnering with communities to enhance malaria control". Nov. 13-18, 2005.
Thera, M; Doumbo, O; Coulibaly, D; Diallo, D; Sagara, I; Heppner, G; Soisson, L; Leach, A; Lyke, K; Plowe, C, "Safety and Immunogenicity of the WRAIR and GSK Biologicals' Malaria Vaccine Candidate AMA-1/AS02A vs. Rabies Vaccine in Adults in Bandiagara, Mali" Nov. 13-18, 2005.
White, C; Kilian, A; Rwakimari, J; Bell, A; Mukasa, V; South, R, "Supporting national community health schemes: initial lessons from the Uganda malaria partnership programme". Nov. 13-18, 2005.
Haaland, A; Kachur, P; Kombe, F; Yaa, F; Barongo, V; Duparc, S; Marsh, V, "Visual instructions promote malaria treatment". Nov. 13-18, 2005.

Cohen J; Alonso, P.L.; Heppner, G.; Ballou, W.R.; Moree, M, "Malaria Vaccines: Not a dream any more". Nov. 13-18, 2005.
Cohen, J; Alonso, P.L.; Heppner, G.; Ballou, W.R.; Moree, M., "The RTS,S malaria vaccine: status and future plans". Nov. 13-18, 2005.
Angov, Evelina, Brent-Kirk, Afiya; Bowden, Scott A; Soisson, Lorraine A; Stoute, Jose A; Ockenhouse, Christian F; Cohen Joe; Diggs, Carter L; Heppner, Donald G(; Lyon, Jeffrey A, "Analysis of antibody specificities detected by an MSP1-42 fragment specific ELISA following vaccination with FMP1/AS02A in three diverse populations". Dec. 11-15, 2005.
Angov, Evelina [Reprint Author]; Khan, Farhat; N-Leitner, Elke S. Bergman; Kincaid, Randall; Heppner, Donald G.; Soisson, Lorraine; Cohen, Joe; Diggs, Carter L.; Lyon, Jeffrey A., "Antibodies raised against Plasmodium falciparum MSP1-42 expressed from a fully codon-harmonized gene are significantly more growth inhibitory than those raised against the same antigen expressed from a partially codon-harmonized gene". Dec. 11-15, 2005.
Kester, Kent E.; Ockenhouse, Chris F.; Krzych, U.; Hall, B.T.; Stewart, V. A.; Williams, J.; Nielsen, R.; Polhemus, M.; Cummings, J. F.; Moran, K.; Magill, A. J.; Moris, P.; Ofori-Anyinam, O.; Dubois, M-C; Garcon, N.; Hanon, E.; Koutsokoukos, M.; Van Mechelen, M.; De Kock, E.; Dehottay, P.; Lievens, M.; Fourneau, M.; Ripley Ballou, W.; Cohen, Joe; Heppner, D. Gray, "Evaluation of a New Formulation of Glaxosmithkline's Candidate Malaria Vaccine RTS,S in the Novel Adjuvant AS01B: Safety, Immunogenicity, and Preliminary Efficacy". Dec. 11-15, 2005.
Shott, Joseph; Pau, Maria Grazia; Demoitiã ©, Marie-Ange; Custers, Jerome H.; McGrath, Shannon; Dubois, Patrice; Ophorst, Olga; Dubois, Marie-Claude; Komisar, Jack; Cohen Joe; Goudsmit, Jaap; Heppner, D. Gray; Stewart, V. Ann, "Evaluation of Immunogenicity of Adenovirus-PfCS Malaria Vaccine Candidates in Mice". Dec. 11-15, 2005.
Walsh, Douglas S.; Gettayacamin, Montip; Lyon, Jeffrey A.; Leitner, Wolfgang W.; Stewart, Ann; Pichyangkul, Sathit; Gosi, Panita; Tongtawe, Pongsri; Holland, Carolyn A.; Kolodny, Nelly; Cohen Joe; Voss, Gerald; Ballou, Ripley; Heppner, D. Gray, Jr, "Heterologous prime-boost immunization with epidermal gene gun administered Plasmodium falciparum circumsporozoite protein (CSP) encoding DNA and intramuscular RTS,S/AS02A in rhesus monkeys generates robust cutaneous delayed-type hypersensitivity responses against CSP C terminus". Dec. 11-15, 2005.
Stewart, V. Ann; McGrath, Shannon M.; Grazia Pau, Maria; Mettens, Pascal; Dubois, Patrice; Custers, Jerome H. H. V.; DemoitiÃ ©, Marie-Ange; Ophorst Olga; Shott, Joseph; Bayat, Babak; Donner, Marie-Noã<<lle; Dubois, Marie-Claude; Goudsmit, Jaap; Cohen, Joe; Heppner, D. Gray, "Heterologous prime-boost with adenovirus35-vectored CS and recombinant protein RTS,S/AS01B greatly enhances immune responses to P. falciparum CS". Dec. 11-15, 2005.
Cobb, Michelle; McGrath, Shannon; Dutta, Sheetij; Ware, Lisa A.; Lalitha, P.V.; Cohen, Joe; Lanar, David E.; Heppner, D. Gray; Stewart, V. Ann, "Interferon-gamma ELISpot responses to PfAMA-1/E, a recombinant protein blood-stage P. falciparum vaccine candidate, in rhesus macaques". Dec. 11-15, 2005.
McGrath, Shannon M.; Bayat, Babak; Donner, Marie-Noã<<lle; Mettens, Pascal; Collignon Catherine; Grazia Pau, Maria; Dubois, Patrice; Goudsmit, Jaap; Cohen, Joe; Heppner, D. Gray; Stewart, V. Ann, "Use of 6-color flow cytometry to measure immune response in rhesus macaques immunized with malaria vaccine candidates". Dec. 11-15, 2005.
Kester, Kent E., "MAL-027: A Phase I/IIa Trial of RTS,S/AS01B vs. RTS,S/AS02A in Adults at the Walter Reed Army Institute of Research". II-Dec. 15, 2005.
ASTMH 55th Annual Meeting book Nov. 12-16, Atlanta, GA. Nov. 13-16, 2006.
Bojang, KA; Olodude, F; Milligan, P; Pinder, M; Vigneron, L; Leach, A; Chilengi, R; Bevilacqua, C; Ofori-Anyinam, O; Fitzpatrick, S; Milman, J; McAdam, KPWJ; Rabinovich, R; Cohen, J; Tornieporth, N, "Safety and Immunogenicity of RTS,S/AS02A Malaria Vaccine in Gambian Children", Abstract Dec. 3, 2003.

(56) References Cited

OTHER PUBLICATIONS

Cohen, J., Development of RTS, S, The Plasmodium Falciparum Recombinant CS Protein Vaccine, No Abstract provided either online or in Abstract book—part of a special symposium so may not be publishedDec. 3, 2003.
Cohen, J. D., "The RTS, S/AS02A Malaria Vaccine Candidate", No Abstract provided either online or in Abstract book Dec. 3, 2003.
Cohen, J D., "Malaria Vaccine Development: a Status Report" No Abstract provided Oct. 17, 2001.
Cohen, Joe, Recent Advances in Malaria Vaccine Development presentation. Abstract. Oct. 7, 2004.
Sun, P; Schwenk, R; Heppner, D G; Krzych, U; Cohen, J. "The Involvement of P Falciparum Protein-Specific CD4+ and CD8+ T Cells in the Protective Immunity Induced by Candidate Malaria Vaccine, RTS,S" Abstract. Jul. 22, 2001.
Holland, C. A.; Williams, J.; Momin, P.; Delchambre, M.; Dubois, M. C.; Watson, E.; Mowery, K.; Tornieporth, N.; Vigneron, L.; Voss, G.; Cohen, J.; Ballou, W. R.; Kester, K. E., Department of Immunology, Walter Reed Army Institute of Research, Washington, DC, USA, American Journal of Tropical Medicine and Hygiene, (Sep. 1999) vol. 61, No. 3 Suppl., pp. 491. print. Meeting Info. Abstract. Nov. 28, 1999.
Sun, PF; Schwenk, R; Palmer, D; Berenzon, D; Stoute, JA; Kester, KE; Cohen, J; Voss, G; Ballou, WR; Heppner, DG, "T lymphocites responses induced by immunization with the candidate Plasmodium falciparum vaccine RTS, S/SBAS2" Am J Trop Med Hyg 2000; 62(3 Suppl.):200-01, Oct. 29-Nov. 2, 2000, Houston, TX. Abstract.
Stewart, V. Ann; McGrath, Shannon; Shott, Joseph; Mettens, Pascal; Grazia Pau, Maria; DuBois, Patrice; Goudsmit, Jaap; Cohen, Joe; Heppner, D. Gray, "Heterologous prime-boost with adenovirus35-vectored CS and recombinant protein RTS,S/AS01 B greatly enhances immune responses to P. falciparum CS" Abstract. Feb. 28, 2006.
Ripley Ballou, W.; Cohen, Joe D., "Recent Progress with the RTS,S Malaria Vaccine", Malaria: Functional Genomics to Biology to Medicine (C5, Feb. 28, 2006, Taos, NM.) Abstract.
Cohen, J, "Malaria: status of the field and the RTS,S vaccine as a case study" Abstract. Aug. 29, 2006.
Stewart, V. Ann; McGrath, Shannon; Grazia Pau, Maria; Mettens, Pascal; Dubois, Patrice M.; Shott, Joseph; Demoitié, Marie-Ange; Bayat, Babak; Donner, Marie-Noëlle; Dubois, Marie-Claude; Goudsmit, Jaap; Cohen, Joe; Gray Heppner, D., "Greatly enhanced immune responses from priming with Adenovirus35-CS followed by RTS,S/AS01B boost in rhesus macaques", Abstract Sep. 17, 2007.
Aponte, John J.; Sacarlal, Jahit; Aide, Pedro; Macete, Eusebio; Renom, Montse; Bassat, Quique; Mandomando, Inacio; Manaca, Maria N.; Lafuente, Sarah; Leach, Amanda; Ballou, Ripley; Lievens, Marc; Thonnard, Joelle; Dubois, Marie-Claude; Demotie, Marie-Ange; Cohen, Joe; Dubovsky, Filip; Millman, Jessica; Sillman, Marla; Alonso, Pedro L., A 4 year follow-up of the safety, immunogenicity and efficacy of the candidate malaria vaccine RTS,S/AS02A in children vaccinated at aged 1 to 4 years in a malaria-endemic region of Mozambique. Abstract Nov. 4, 2007.
Aponte, John J.; Aide, Pedro; Renom, Montse; Mandomando, Inacio; Bassat, Quique; Sacarlal, Jahit; Manaca, Maria N.; Lafuente, Sarah; Macete, Eusebio; Leach, Amanda; Ballou, Ripley; Lievens, Marc; Vekemans, Johan; Dubois, Marie-Claude; Demotie, Marie-Ange; Cohen, Joe; Dubovsky, Filip; Millman, Jessica; Sillman, Marla; Alonso, Pedro L., A Phase I/IIb randomized, double-blind, controlled clinical trial of the safety, immunogenicity and efficacy of RTS,S/AS02D, a candidate malaria vaccine in Mozambican infants. Abstract Nov. 4, 2007.
Lell, Bertand; Agnandji, Selidji; von Glasenapp, Isabelle; Oyakhiromen, Sunny; Haertle, Sonja; Kremsner, Peter G.; Ramboer, Isabelle; Lievens, Marc; Ballou, Ripley; Vekemans, Johan; Dubois, Marie-Claude; Demoitie, Marie-Ange; Cohen, Joe; Villafana, Tonya; Carter, Terrell; Petersen, Carolyn, "A randomized, observer-blind trial to compare safety and immunogenicity of two adjuvanted RTS,S anti-malaria vaccine candidates in Gabonese children". Abstract Nov. 4, 2007.

Barbosa, Arnoldo; Naniche, Denise; Manaca, Maria N.; Aponte, John; Mandomando, Inacio; Aide, Pedro; Renom, Montse; Sacarlal, Jahit; Ballou, Ripley; Moris, Philippe; Cohen, Joe; Dubovsky, Filip; Millman, Jessica; Alonso, Pedro L., "Assessment of cellular immune responses in infants participating in a RTS,S/AS02D phase I/IIb trial in Mozambique". Abstract Nov. 4, 2007.
Barbosa, Arnoldo; Naniche, Denise; Manaca, Maria N.; Aponte, John; Mandomando, Inacio; Aide, Pedro; Renom, Montse; Sacarlal, Jahit; Ballou, Ripley; Moris, Philippe; Cohen, Joe; Dubovsky, Filip; Millman, Jessica; Alonso, Pedro L., "Assessment of cellular immune responses in infants participating in a RTS,S/AS02D phase I/IIb trial in Mozambique". Nov. 4, 2007.
Anyona, Samuel B.; Hunja, Carol W.; Kifude, Carolyne M.; Polhemus, Mark E.; Gray Heppner, D.; Leach, Amanda; Lievens, Marc; Ballou, Ripley; Cohen, Joe; Sutherland, Colin; Waitumbi, John N., "Impact of RTS,S/AS02A and RTS,S/AS01B on Multiplicity of Infections and CSP T-cell Epitopes of P. falciparum in Adults Participating in a Malaria Vaccine Clinical Trial". Abstract Nov. 4, 2007.
Pichyangkul, Sathit; Kum-Arb, Utaiwan; Yongvanitchit, Kosol; Limsalakpetch, Amporn; Gettayacamin, Monthip; Lanar, David E.; Ware, Lisa A.; Stewart, V. A.; Gray Heppner, D.; Mettens, Pascal; Cohen, Joe D.; Ballou, W. R.; Fukuda, Mark M., "Pre-clinical evaluation of safety and immunogenicity of Plasmodium falciparum LSA1/AS01B when administered separately or concurrently with RTS,S/AS01B in rhesus primates". Abstract Nov. 4, 2007.
Aponte, John J.; Sacarlal, Jahit; Aide, Pedro; Macete, Eusebio; Renom, Montse; Bassat, Quique; Mandomando, Inacio; Manaca, Maria N.; Lafuente, Sarah; Leach, Amanda; Ballou, Ripley; Lievens, Marc; Thonnard, Joelle; Dubois, Marie-Claude; Demotie, Marie-Ange; Cohen, Joe; Dubovsky, Filip; Millman, Jessica; Sillman, Marla; Alonso, Pedro L, "A Four-Year Follow-Up of the Safety, Immunogenicity and Efficacy of the Candidate Malaria Vaccine RTS,S/AS02A in Children Vaccinated at Aged 1 to 4 Years in a Malaria-Endemic Region of Mozambique". Abstract Nov. 4, 2007.
von Glasenapp, I.; Lell, B.; Agnandji, S.; Oyakhiromen, S.; Haertle, S.; Kremsner, P.G.; Carter, T.; Sillman, M.; Villafana, T.; Lievens, M.; Vekemans, J.; Leach, A.; Dubois, M.C.; Demoitie, M.A.; Cohen, J.; Ballou, R., "AS01 and AS02 Adjuvanted RTS,S Anti-Malaria Vaccine Candidates: Safety and Immunogenicity in Children in Gabon". Abstract May 13, 2008.
Cohen, Joe, "The RTS,S. Malaria Vaccine Candidate: From Phase II to Phase III" Abstract Jun. 8, 2008.
Owusu-Agyei, Seth; Ansong, D.; Asante, K. P.; Owusu-Kwarteng, S.; Owusu, R.; Wireko Brobby, N.A.; Dosoo, D.; Osei Akoto, A. Y.; Osei-Kwakye, K.; Asafo Adjei, E.; Owusu Boahen, K.; Sylverken, J.; Adjei, G.; Sambian, D.; Vekemans, J.; Ofori-Anyinam, O.; Lievens, M.; Demoitie, M.; Cohen, J.; Ballou, W. R.; Savarese, B.; Greenwood, B.; Bawa, T.; Evans, J.; Agbenyega, T., "Phase II, Randomized Trial to Assess the Safety and Immunogenicity of the Candidate Malaria Vaccines RTS,S/AS02 and RTS,S/AS01 When Given According to Different Vaccination Schedules in Children in Ghana". Abstract Dec. 7, 2008.
Bejon, P.; Lusingu, J.; Olotu, Ally; Leach, A.; Lievens, M.; Vekemans, J.; Msham, S.; Lang, T.; Gould, J.; Dubois, M.C.; Demoitie, M.A.; Vansadia, P.; Carter, T.; Njuguna, P.; Kawuondo, K.; Gesase, S.; Drakeley, C.; Savarese, B.; Villafana, T.; Ballou, W. R.; Cohen, J.; Riley, E.; Lemnge, M.; Marsh, K.; von Seidlein, L., "Phase IIb, Randomized, Double-Blind Trial to Assess the Efficacy, Safety and Immunogenicity of the Candidate Malaria Vaccine RTS,S/AS01 in Kenyan and Tanzanian Children". Abstract Dec. 7, 2008.
Abdulla, Salim; Oberholzer, R.; Juma, O.; Leach, A.; Vekemans, J.; Lievens, M.; Kuboja, S.; Salim, N.; Carter, T.; Demoitie, M.A.; Dubois, M.C.; Jumanne, A.; Machel, F.; Membi, C.; Shomari, M.; Aebi, T.; Mshinda, H.; Villafana, T.; Cohen, J.; Ballou, W. R.; Tanner, M., "Phase IIb, Randomized, Double-Blind Trial to Assess the Safety, Immunogenicity and Efficacy of the Candidate Malaria Vaccine RTS,S/AS02 When Administered According to the Expanded Program on Immunization Schedule". Abstract Dec. 7, 2008.
Cohen, J, "The vaccine RTS,S/AS: from the original insight to the development of the most promising candidate". Abstract Sep. 6, 2009.

(56) References Cited

OTHER PUBLICATIONS

Cohen, J., "The RTS,S Malaria Vaccine candidate: Getting closer to the goal", Abstract Oct. 4, 2009.

Agnandji, Selidji T; Poku Asante, Kwaku; Lyimo, John; Vekemans, Johan; Soulanoudjingar, Solange S; Owusu, Ruth; Shomari, Mwanajaa; Leach, Amanda; Fernandes, Jose; Dosoo, David; Chikawe, Maria; Issifou, Saadou; Osei-Kwakye, Kingsley; Lievens, Marc; Paricek, Maria; Apanga, Stephen; Mwangoka, Grace; Dubois, Marie-Claude; Okissi, Blaise; Kwara, Evans; Minja, Rose; Lange, Jörn; Boahen, Owusu; Kayan, Kingsley; Adjei, George; Chandramohan, Daniel; Carter, Terrell; Vansadia, Preeti; Villafana, Tonya; Sillman, Marla; Savarese, Barbara; Lapierre, Didier; Greenwood, Brian; Tanner, Marcel; Cohen, Joe; Kremsner, Peter; Lell, Bertrand; Owusu Agyei, Seth; Abdulla, Salim, "Randomized, controlled Phase 2 study assessing the safety and immunogenicity of the RTS,S/AS01E candidate malaria vaccine, when incorporated into an EPI regimen including DTPwHepB/Hib, OPV, measles and yellow fever vaccination". Abstract Nov. 2, 2009.

Lumsden, Joanne; Schwenk, Robert J.; Egner, Lisa; Cohen, Joe; Ballou, Ripley; Ofori-Anyinam, Opokua; Moris, Philippe; Kester, Kent E.; Gray Heppner, D.; Krzych, Urszula, "IL-2 Producing Effector Memory and Central Memory CD4+T cell Subsets Are Associated with Protective Immunity in RTS,S-Immunized Subjects". Nov. 18, 2009.

Pichyangkul, S.; Tongtawe, P.; Kum-Arb, U.; Yongvanitchit, K.; Gettayacamin, M.; Hollingdale, M. R.; Limsalakpetch, A.; Heppner, D. G.; Cohen, J. D.; Bergmann-Leitner, E. S.; Ware, L. A.; Angov, E.; Dutta, S.; Lanar, D. E.; Stewart, V. A. Evaluation of the safety and immunogenicity of Plasmodium falciparum apical membrane antigen 1, merozoite surface protein 1 or RTS,S vaccines with adjuvant system $AS02_A$ administered alone or concurrently in rhesus monkeys. Abstract Aug. 22, 2010.

Asante, Kwaku Poku; Abdulla, Salim; Agnandji, Selidji; Lyimo, John; Vekemans, Johan; Soulanoudjingar, Solange; Owusu, Ruth; Shomari, Mwanajaa; Leach, Amanda; Salim, Nahya; Fernandes, Jose; Dosoo, David; Chikawe, Maria; Issifou, Saadou; Osei-Kwakye, Kingsley; Lievens, Marc; Paricek, Maria; Möller, Tina; Apanga, Stephen; Mwangoka, Grace; Dubois, Marie-Claude; Tigani, Madi; Okissi, Blaise; Kwara, Evans; Minja, Rose; Lange, Jorn; Houkpatin, Aurore; Boahen, Owusu; Kayan, Kingsley; Adjei, George; Chandramohan, Daniel; Carter, Terrell; Vansadia, Preeti; Sillman, Marla; Savarese, Barbara; Lapierre, Didier; Greenwood, Brian; Cohen, Joe; Kremsner, Peter; Agyei, Seth Owusu; Tanner, Marcel; Lell, Bertrand; Safety, immunogenicity and efficacy of the RTS,S/$AS01_E$ malaria vaccine candidate integrated in EPI: extended follow-up of a randomized controlled Phase 2 infant trial in Gabon, Ghana and Tanzania. Abstract Nov. 3, 2010.

\* cited by examiner

Figure 1 – CD4 T Cells Response Against CSP (First Cohort)
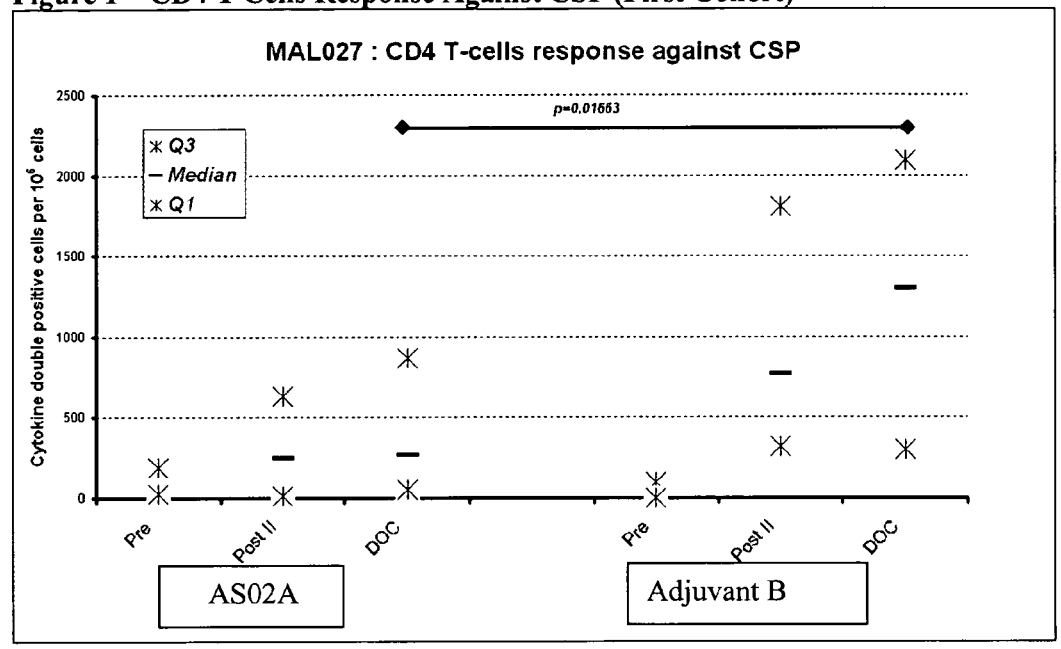

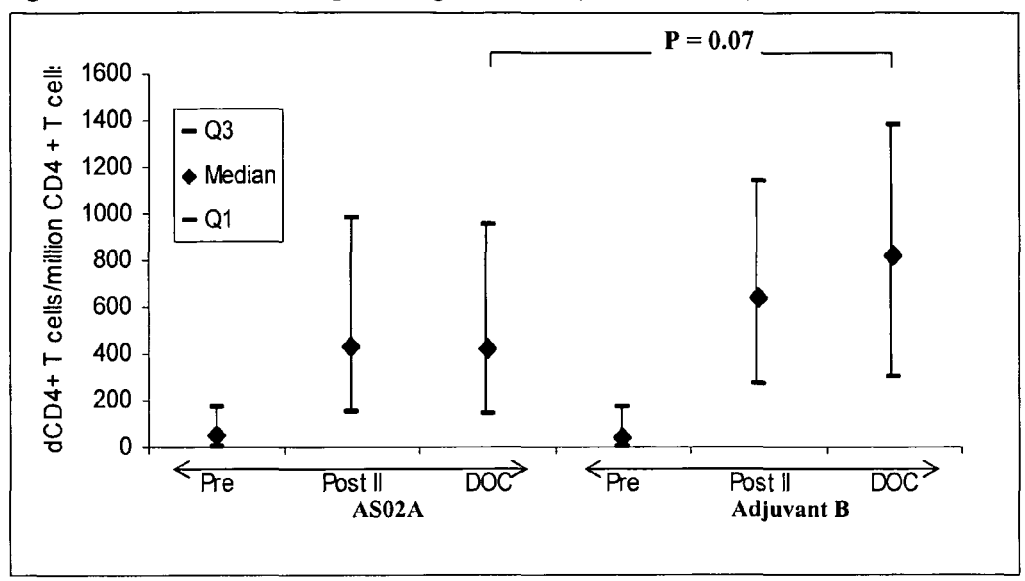
Figure 2 – CD4 T Cells Response Against CSP (Both Cohorts)

Figure 3 – CD4 T Cells Response Against CSP (First Cohort)
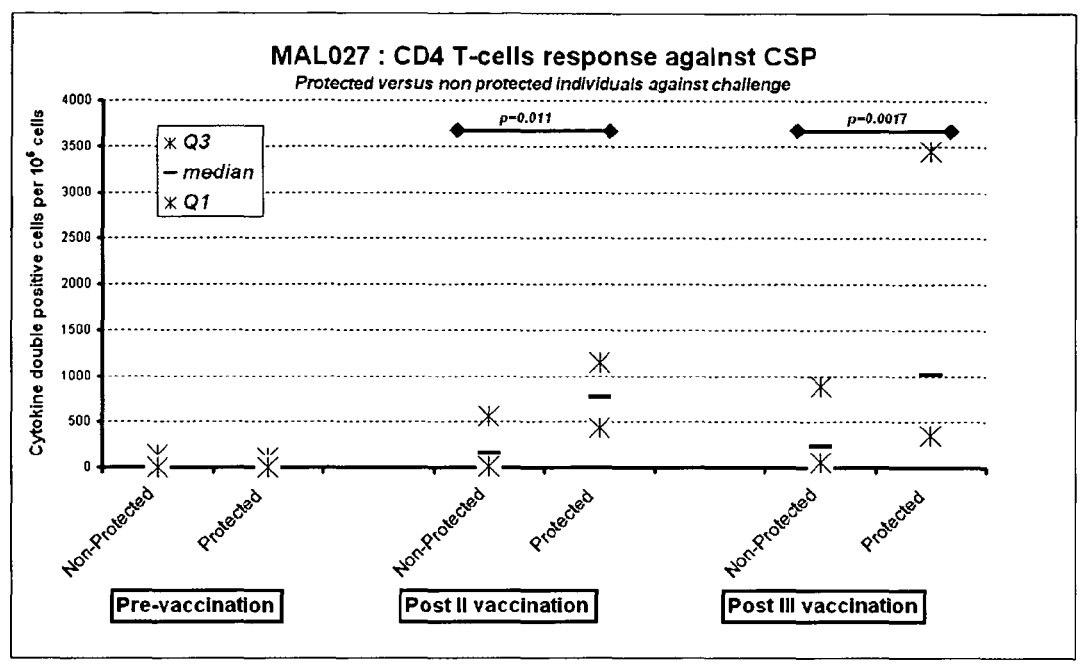

Figure 4 – CD4 T Cells Response Against CSP (Both Cohorts)
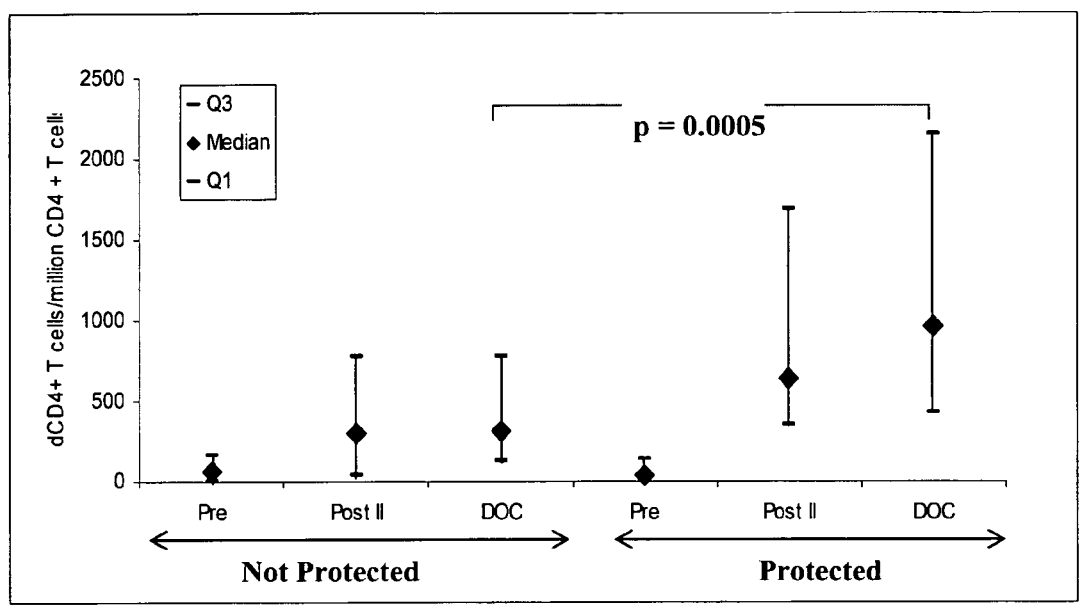

Figure 5 – Anti-CSP Antibody Response (Both Cohorts)
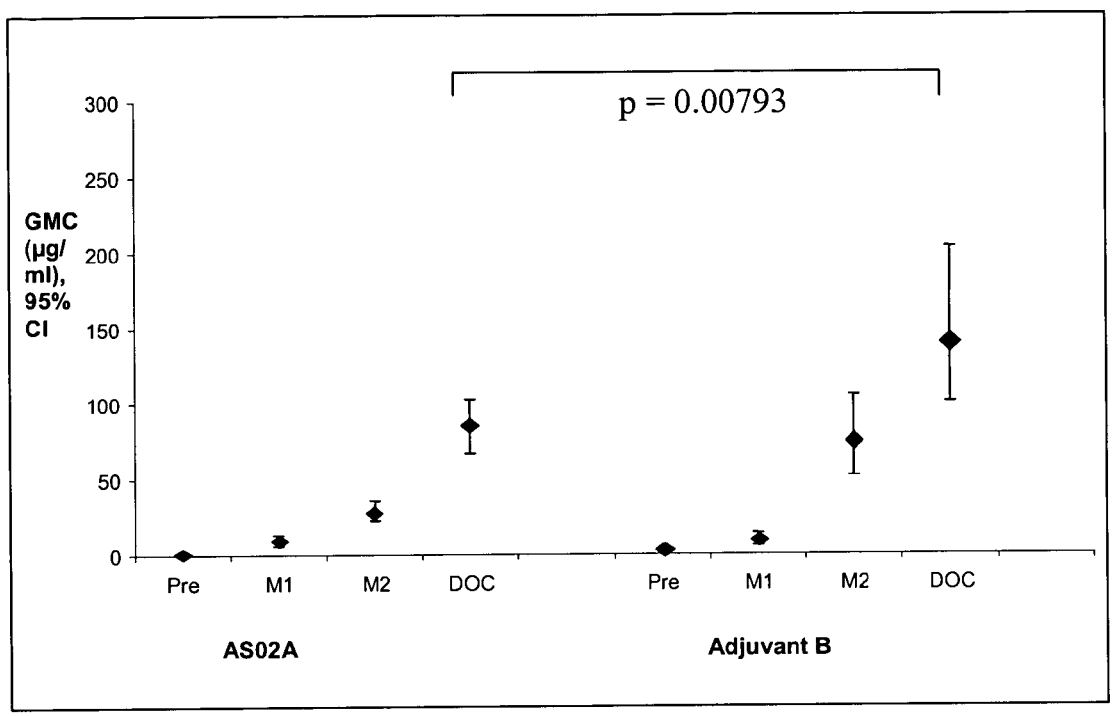

Figure 6 - Anti-CSP Antibody Response (Both Cohorts)
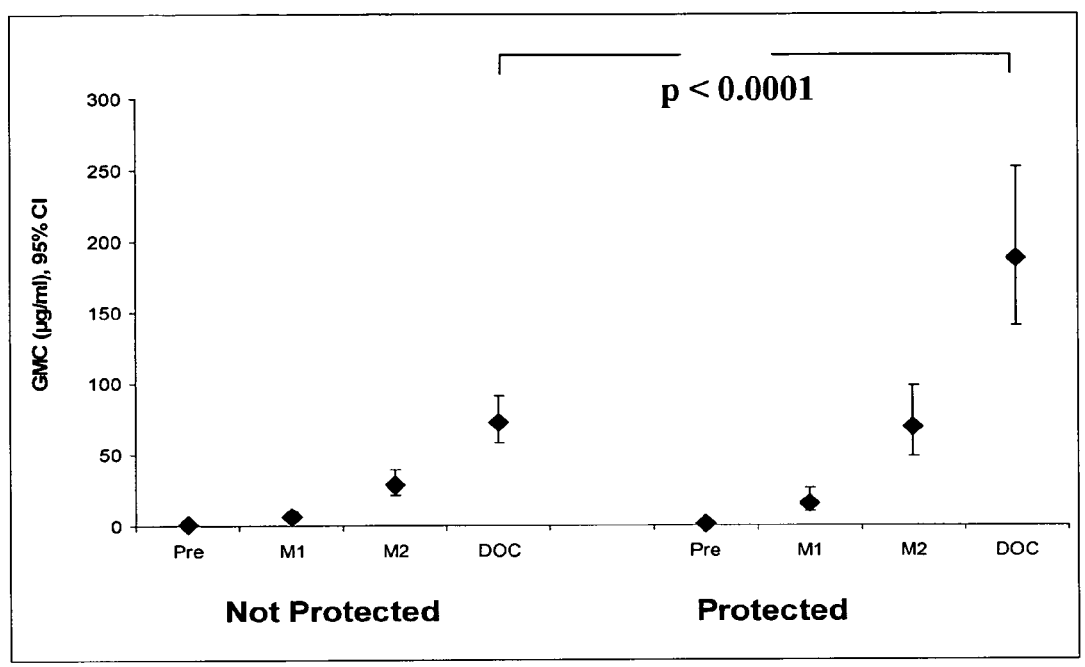

```
SEQUENCE LISTING

<160> NUMBER OF SEQ ID NOS: 3

<210> SEQ ID NO 1
<211> LENGTH: 4
<212> TYPE: PRT
<213> ORGANISM: Plasmodium falciparum

<400> SEQUENCE: 1

Asn Ala Asn Pro
1

<210> SEQ ID NO 2
<211> LENGTH: 4
<212> TYPE: PRT
<213> ORGANISM: Plasmodium falciparum

<400> SEQUENCE: 2

Asn Val Asp Pro
1
```

```
<210> SEQ ID NO 3
<211> LENGTH: 4
<212> TYPE: PRT
<213> ORGANISM: Hepatitis B virus

<400> SEQUENCE: 3

Pro Val Thr Asn
1
```

ANTI-MALARIA VACCINE

CROSS-REFERENCE TO RELATED APPLICATIONS

This application is the US National Stage of International Application No. PCT/EP2006/006407, filed 29 Jun. 2006, which is incorporated herein by reference. This application also claims benefit of the filing date of GB 0513421.8, filed 30 Jun. 2005.

BACKGROUND OF THE INVENTION (1) Field of the Invention

The present invention relates to a novel use of a malaria antigen to immunise against malaria infection and disease. The invention relates in particular to the use of sporozoite antigens, in particular circumsporozoite (CS) protein or immunogenic fragments or derivatives thereof, combined with suitable adjuvants, to immunise malaria naïve individuals expecting to travel to endemic regions against malaria infection.

(2) Description of the Related Art

Malaria is one of the world's major health problems. During the 20th century, economic and social development, together with anti-malarial campaigns, have resulted in the eradication of malaria from large areas of the world, reducing the affected area of the earth's land surface from 50% to 27%. Nonetheless, given expected population growth it is projected that by 2010 half of the world's population, nearly 3.5 billion people, will be living in areas where malaria is transmitted (Hay, 2004). Current estimates suggest that there are well in excess of 1 million deaths due to malaria every year, and the economic costs for Africa alone are staggering (Bremen, 2004).

These figures highlight the global malaria crisis and the challenges it poses to the international health community. The reasons for this crisis are multiple and range from the emergence of widespread resistance to available, affordable and previously highly effective drugs, to the breakdown and inadequacy of health systems and the lack of resources. Unless ways are found to control this disease, global efforts to improve health and child survival, reduce poverty, increase security and strengthen the most vulnerable societies will fail.

Malaria also poses risks to those traveling to or working in endemic regions who normally live in malaria free countries. The risks may be greater to this traveler population because they do not have any background immunity to malaria from natural exposure. Another aspect of the risk incurred by a traveler to a malaria endemic region is that the disease is often mis-diagnosed in its early stages due to the flu-like symptoms. When the severity increases and malaria is finally diagnosed, it can be too late. Within a few days of the increased symptoms, death can result, for example, from cerebral malaria, or sometimes organ (e.g. liver or kidney) failure.

One of the most acute forms of the disease is caused by the protozoan parasite *Plasmodium falciparum* which is responsible for most of the mortality attributable to malaria. Another form of the disease is caused by *Plasmodium vivax*. *P. vivax* is the most widespread of all malarias. In addition to being present in tropical and sub-tropical regions, the ability of the parasite to complete its mosquito cycle at temperatures as low as 15 degrees Celsius, has allowed it to spread in temperate climates. However due to the fact that *P. vivax* infection is rarely fatal, the efforts to control *P. vivax* malaria (through vaccine development) are lagging behind those for *P. falciparum*.

An observation made 30 years ago provides strong support for the belief that an effective malaria vaccine will eventually be developed. Mice and humans can be protected against malaria by immunisation with live, radiation-attenuated malaria sporozoites. The persistence of intra-hepatic stage in vivo is required to produce and maintain protective immunity, but the underlying mechanisms have not yet been completely defined. Antibodies, CD8 and CD4 T-cells (Hoffman, 1996) have been implicated as critical effector immune mediators.

The life cycle of *Plasmodium* sp (eg, *P. falciparum* or *P. vivax*) is complex, requiring two hosts, man and mosquito for completion. The infection of man is initiated by the inoculation of sporozoites in the saliva of an infected mosquito. The sporozoites migrate to the liver and there infect hepatocytes (liver stage) where they differentiate, via the exoerythrocytic intracellular stage, into the merozoite stage which infects red blood cells (RBC) to initiate cyclical replication in the asexual blood stage. The cycle is completed by the differentiation of a number of merozoites in the RBC into sexual stage gametocytes which are ingested by the mosquito, where they develop through a series of stages in the midgut to produce sporozoites which migrate to the salivary gland.

The sporozoite stage of *Plasmodium* sp (eg, *P. falciparum* or *P. vivax*) has been identified as one potential target of a malaria vaccine. The major surface protein of the sporozoite is known as circumsporozoite protein (CS protein). This protein has been cloned, expressed and sequenced for a variety of strains, for example for *P. falciparum* the NF54 strain, clone 3D7 (Caspers, 1989). The protein from strain 3D7 is characterised by having a central immunodominant repeat region comprising a tetrapeptide Asn-Ala-Asn-Pro (SEQ ID NO:1) repeated 40 times but interspersed with four minor repeats of the tetrapeptide Asn-Val-Asp-Pro (SEQ ID NO:2). In other strains the number of major and minor repeats varies as well as their relative position. This central portion is flanked by an N and C terminal portion composed of non-repetitive amino acid sequences designated as the repeatless portion of the CS protein.

GlaxoSmithKline Biologicals' RTS,S malaria vaccine based on CS protein has been under development since 1987 and is currently the most advanced malaria vaccine candidate being studied (Ballou, 2004). This vaccine specifically targets the pre-erythrocytic stage of *P. falciparum*.

RTS,S/AS02A (RTS,S plus adjuvant AS02A which contains immunostimulants QS21, 3D-MPL and an oil in water emulsion) was used in consecutive Phase I studies undertaken in The Gambia involving adults (Doherty, 1999), children aged 6-11 and 1-5 years (Bojang, 2005), which confirmed that the vaccine was safe, well-tolerated and immunogenic. Subsequently a paediatric vaccine dose was selected and studied in a Phase I study involving Mozambican children aged 1-4 years where it was found to be safe, well tolerated and immunogenic (Macete).

The RTS,S/AS02A vaccine has also shown evidence of efficacy in clinical trials in the USA and in the field in West Africa. RTS,S/AS02A induces significant IgG antibody responses to *P. falciparum* circumsporozoite protein and substantial T-cell immunity (Lalvani, 1999; Sun, 2003). Efficacy against *P. falciparum* experimental challenge in malaria-naïve volunteers in the USA has been estimated to be about 30-50% on average (Stoute, 1997; Stoute 1998; Kester, 2001). The first of these studies (Stoute, 1997) was 86% effective in a small scale trial in which 6 out of 7 individuals immunized with RTS,S/AS02A were protected. Furthermore, a field study of semi-immune adults in The Gambia (preceeded by a safety study in Gambian adults (Doherty, 1999)) showed an overall efficacy of 34% over a period of one transmission season of 15 weeks, with 71% efficacy in the first nine weeks of follow-up and 0% efficacy thereafter (Bojang, 2001). These studies (Stoute, 1997; Stoute, 1998; Bojang, 2001; Kester, 2001) show efficacy against infection.

Results were recently reported from a trial using RTS,S/AS02A in young African children. It was discovered that the CS protein based RTS,S vaccine can confer not only protection against infection under natural exposure but also protection against a wide spectrum of clinical illness caused by *P. falciparum*. Children who received the RTS,S vaccine experienced fewer serious adverse events, hospitalisations, and severe complications from malaria, including death, than did those in the control group (Alonso, 2004).

Furthermore, the RTS,S vaccine efficacy against both new infections or clinical episodes appears either not to wane or to do so slowly. At the end of the 6 months follow up in the trial, the vaccine remained efficacious as there was a significant difference in the prevalence of infection. This is in contrast with previous trials in malaria naïve volunteers or Gambian adults which suggested that vaccine efficacy with RTS,S was short lived (Stoute, 1998; Bojang, 2001). Furthermore, after an additional follow-up period of 12 months, it was observed that the efficacy of the vaccine against an episode of clinical malaria did not significantly wane (Alonso, 2005).

Although the vaccine formulation described above shows clinical efficacy, additional improvements are still needed in order to increase both the number of individuals protected as well as the persistence of protection. New adjuvant formulations such as a formulation which contains QS21 and 3D-MPL in a liposome containing formulation (referred to herein as adjuvant B) have demonstrated a higher potency to boost T-cell immune response in various pre-clinical and clinical investigations.

In particular, what is needed for a vaccine for people who do not come from a malaria endemic region but are traveling for a limited period of time to regions where malaria is endemic, is better protection against infection. Clinical manifestation of malaria can only occur if there is a productive infection of the liver leading to the formation of merozoites and their release from the hepatic stage. These merozoites can then infect RBC and initiate the pathogenic blood stage of the parasite resulting in symptomatic clinical malaria. If there is no productive infection following exposure (i.e. no infection of the liver and/or no release of liver merozoites), then this is known as sterile immunity. A vaccine that would significantly reduce the risk of a productive liver infection, as defined above, following mosquito bites would be highly desirable for a traveler population that does not have pre-existing immunity, because by preventing the productive hepatic infection the vaccine would prevent any subsequent clinical manifestation. This can be contrasted with the aim of vaccine development targeting children or people in endemic regions, where the major aim would be to decrease the severity of disease and/or to decrease the number of episodes of disease, but not necessarily to prevent them completely. In theory, it would not be possible to indefinitely maintain sterile protection in people in endemic regions, and therefore they need to build up their own immunity by exposure to malaria infection. Furthermore, it may not be advisable to confer sterile protection on people living in endemic regions for an extended yet limited period of time.

We describe herein a challenge clinical trial consisting of a head to head comparison of RTS,S/AS02A versus RTS,S with a different adjuvant (adjuvant B) which contains QS21 and 3D-MPL in a formulation with cholesterol-containing liposomes, in a malaria naïve population (see Examples). Both T- and B-cell mediated immunity were investigated.

The results show that in a malaria naïve adult population the RTS,S antigen in combination with adjuvant B is greater than 50% more effective at protecting against productive hepatic infection following malaria challenge than RTS,S/AS02A. Thus, the RTS,S antigen in combination with adjuvant B is more effective in terms of the sterile protection which is required for malaria naïve individuals traveling to regions where malaria is endemic. This increased efficacy conferred by adjuvant B is associated with an increased antigen specific immune response (antibodies and CD4-Th1 T-cells).

BRIEF DESCRIPTION OF THE DRAWINGS

FIG. 1 shows the CD4+ T cell response against CSP in the first cohort comparing adjuvant ASO2A with Adjuvant B.

FIG. 2 shows the CD4+ T cell response against CSP in both cohorts comparing adjuvant ASO2A with Adjuvant B.

FIG. 3 shows the double cytokine positive CD4+ T cell response against CSP in both cohorts comparing the responses in protected and unprotected subjects after each vaccination.

FIG. 4 shows the CD4+ T cell response against CSP in both cohorts comparing the responses in protected and unprotected subjects.

FIG. 5 shows the anti-CSP antibody response in both cohorts with comparing adjuvant ASO2A with Adjuvant B.

FIG. 6 shows the anti-CSP antibody response in both cohorts comparing the responses in protected and unprotected subjects.

DETAILED DESCRIPTION OF THE INVENTION

Therefore the present invention provides the use of a *Plasmodium* antigen or an immunogenic fragment or derivative thereof and an adjuvant comprising a lipid A derivative and a saponin in a liposome formulation, in the manufacture of a medicament for immunising travelers to endemic regions against productive malaria infection.

Generally, travelers to endemic regions will be malaria naïve. Thus, the invention applies to malaria naïve individuals.

The invention is particularly concerned with reducing the incidence of productive malaria infections in travelers to endemic regions, who may be any age but in particular adults.

A second aspect of the invention provides a formulation comprising a *Plasmodium* antigen or an immunogenic fragment or derivative thereof and an adjuvant, comprising a lipid A derivative and a saponin in a liposome formulation, for use in the immunisation of travelers to endemic regions against productive malaria infection.

A third aspect of the invention provides a method of prophylaxis of productive malaria infection in travelers to endemic regions comprising the administration of suitable amounts of a formulation comprising a *Plasmodium* antigen or an immunogenic fragment or derivative thereof and an adjuvant, comprising a lipid A derivative and a saponin in a liposome formulation.

In one embodiment of the invention the *Plasmodium* antigen is a *P. falciparum* antigen. In another embodiment of the invention the *Plasmodium* antigen is a *P. vivax* antigen.

Suitably the antigen is a pre-erythrocytic antigen.

The antigen may for example be selected from any antigen which is expressed on the sporozoite or other pre-erythrocytic stage of the parasite such as the liver stage. For example the antigen may be selected from circumsporozoite (CS) protein, liver stage antigen-1 (LSA-1) (see eg WO2004/044167), liver stage antigen-3 (LSA-3) (described e.g. in EP 0 570 489 and EP 0 833 917), Pfs 16 kD (described in WO 91/18922 and EP 597 843), Exported antigen-1 (Exp-1) (described for example in Meraldi et al 2002, Parasite Immunol vol 24(3):141), sporozoite-threonine-asparagine-rich protein (STARP), sporozoite and liver stage antigen (SALSA), thrombospondin related anonymous protein (TRAP) (described in WO 90/01496, WO 91/11516 and WO 92/11868) and apical merezoite antigen-1 (AMA-1) (described in EP 0 372 019) which has recently been shown to be present at the liver stage (in addition to the erythrocytic stage). All of these antigens are well known in the field. The antigen may be the entire protein or an immunogenic fragment thereof or a derivative of either of these. Immunogenic fragments of malaria antigens are well know, for example the ectodomain from AMA-1 (described e.g. in WO 02/077195). Derivatives include for example fusions with other proteins which may be malaria proteins or non-malaria proteins such as HBsAg. Derivatives according to the invention are capable of raising an immune response against the native antigen.

The *Plasmodium* antigen may be fused to the surface antigen from hepatitis B (HBsAg).

One particular antigen for use in the invention is derived from the circumsporozoite (CS) protein and may be in the form of a hybrid protein with HBsAg. The antigen may be the entire CS protein or part thereof, including a fragment or fragments of the CS protein which fragments may be fused together.

The CS protein based antigen may be in the form of a hybrid protein comprising substantially all the C-terminal portion of the CS protein of *Plasmodium*, four or more tandem repeats of the CS protein immunodominant region, and the surface antigen from hepatitis B (HBsAg). The hybrid protein may comprise a sequence which contains at least 160 amino acids and which is substantially homologous to the C-terminal portion of the CS protein. In particular "substantially all" the C terminal portion of the CS protein includes the C terminus devoid of the hydrophobic anchor sequence. Further, in the case of the antigen from *Plasmodium falciparum*, it contains 4 or more eg 10 or more Asn-Ala-Asn-Pro (SEQ ID NO:1) tetrapeptide repeat motifs. The CS protein may be devoid of the last 12 amino-acids from the C terminal.

The hybrid protein for use in the invention may be a protein which comprises a portion of the CS protein of *P. falciparum* substantially as corresponding to amino acids 207-395 of *P. falciparum* 3D7 clone, derived from the strain NF54 (Caspers, 1989) fused in frame via a linear linker to the N-terminal of HBsAg. The linker may comprise a portion of preS2 from HBsAg.

CS constructs for use in the present invention are as outlined in WO 93/10152. One particular construct is the hybrid protein known as RTS as described in WO 93/10152 (wherein it is denoted RTS*) and WO 98/05355, the whole contents of both of which are incorporated herein by reference.

A particular hybrid protein for use in the invention is the hybrid protein known as RTS which consists of:

A methionine-residue, encoded by nucleotides 1059 to 1061, derived from the *Sacchromyes cerevisiae* TDH3 gene sequence. (Musti, 1983).

Three amino acids, Met Ala Pro, derived from a nucleotide sequence (1062 to 1070) created by the cloning procedure used to construct the hybrid gene.

A stretch of 189 amino acids, encoded by nucleotides 1071 to 1637 representing amino acids 207 to 395 of the circumsporozoite protein (CSP) of *Plasmodium falciparum* strain 3D7 (Caspers, 1989).

An amino acid (Gly) encoded by nucleotides 1638 to 1640, created by the cloning procedure used to construct the hybrid gene.

Four amino acids, Pro Val Thr Asn, encoded by nucleotides 1641 to 1652, and representing the four carboxy terminal residues of the hepatitis B virus (adw serotype) preS2 protein (Valenzuela, 1979).

A stretch of 226 amino acids, encoded by nucleotides 1653 to 2330, and specifying the S protein of hepatitis B virus (adw serotype).

The RTS may be in the form of RTS,S mixed particles.

The RTS,S particles comprise two polypeptides RTS and S that may be synthesized simultaneously and spontaneously form composite particulate structures (RTS,S) e.g. during purification.

The RTS protein may be expressed in yeast, for example *S. cerevisiae*. In such a host, RTS will be expressed as lipoprotein particles. The recipient yeast strain may already carry in its genome several integrated copies of an hepatitis B S expression cassette. The resulting strain synthesizes therefore two polypeptides, S and RTS, that spontaneously co-assemble into mixed (RTS,S) lipoprotein particles. These particles may present the CSP sequences of the hybrid at their surface. The RTS and S in these mixed particles may be present at a particular ratio, for example 1:4.

The use of a further malaria antigen or fragment or derivative thereof in the invention is also encompassed within the invention. Other pre-erythrocytic antigens such as AMA-1, LSA-1, LSA-3 (described e.g. in EP 0 570 489 and EP 0 833 917) and Pfs 16 kD, may be used in combination with RTS,S. Alternatively RTS,S may be used in combination with a blood stage antigen such as merezoite surface protein-1 (MSP-1) (described e.g. in U.S. Pat. No. 4,837,016), erythrocyte binding antigen-175 (EBA-175) or MSP-3 (described e.g. in EP 0 666 916).

Immunogenic fragments of any of the antigens as described herein will contain at least one epitope of the antigen and display malaria antigenicity and are capable of raising an immune response when presented in a suitable construct, such as for example when fused to other malaria antigens or other non-malaria antigens, or presented on a carrier, the immune response being directed against the native antigen. Typically the immunogenic fragments contain at least 20, or at least 50, or at least 100 contiguous amino acids from the malaria antigen.

Derivatives of the antigens or fragments as described herein will similarly contain at least one epitope of the antigen and display malaria antigenicity and are capable of raising an immune response, the immune response being directed against the native antigen. Derivatives include for example fusions of the malaria antigen to another protein which may or may not be another malaria protein and may be, for example, HBsAg.

In accordance with the invention, an aqueous solution of the purified hybrid protein may be used directly and combined with the suitable adjuvant according to the invention. Alternatively, the protein can be lyophilized prior to mixing with the adjuvant. The adjuvant may be a liquid and is thus used to reconstitute the antigen into a liquid vaccine form.

Thus the invention further provides the use of a *Plasmodium* antigen or an immunogenic fragment or derivative thereof and an adjuvant comprising a lipid A derivative and a saponin in a liposome formulation, as described herein, in the manufacture of a kit for immunising travelers to endemic regions against malaria infection, wherein the antigen is provided in lyophilised form and the antigen and the adjuvant are mixed prior to administration.

The vaccine dose in accordance with the invention may be between 1-100 ug RTS,S per dose, for example 25 to 75 ug RTS,S, for example a dose of 50 ug RTS,S protein, which may be present in 500 ul (final liquid formulation).

This is a suitable dose for use in adults. A suitable dose for use in children is half the adult dose, that is 25 ug RTS,S, which may be present in 250 ul (final liquid formulation). Similar doses may be used for other antigens.

In accordance with the invention the antigen is combined with an adjuvant which comprises a lipid A derivative and a saponin in a liposome formulation.

Suitable adjuvants according to the invention are detoxified lipid A from any source and non-toxic derivatives of lipid A, which are preferential stimulators of a Th1 cell response (also herein called a Th1 type response).

An immune response may be broadly divided into two extreme categories, being a humoral or cell mediated immune response (traditionally characterised by antibody and cellular effector mechanisms of protection respectively). These categories of response have been termed Th1-type responses (cell-mediated response), and Th2-type immune responses (humoral response).

Extreme Th1-type immune responses may be characterised by the generation of antigen specific, haplotype restricted cytotoxic T lymphocytes, and natural killer cell responses. In mice Th1-type responses are often characterised by the generation of antibodies of the IgG2a subtype, whilst in the human these correspond to IgG1 type antibodies. Th2-type immune responses are characterised by the generation of a range of immunoglobulin isotypes including in mice IgG1.

It can be considered that the driving force behind the development of these two types of immune responses are cytokines. High levels of Th1-type cytokines tend to favour the induction of cell mediated immune responses to the given antigen, whilst high levels of Th2-type cytokines tend to favour the induction of humoral immune responses to the antigen.

The distinction of Th1 and Th2-type immune responses is not absolute, and can take the form of a continuum between these two extremes. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, 1989). Traditionally, Th1-type responses are associated with the production of the INF-gamma cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10 and tumour necrosis factor-beta (TNF-beta).

It is known that certain vaccine adjuvants are particularly suited to the stimulation of either Th1 or Th2-type cytokine responses. Traditionally, indicators of the Th1:Th2 balance of the immune response after a vaccination or infection include direct measurement of the production of Th1 or Th2 cytokines by T lymphocytes in vitro after restimulation with antigen, and/or the measurement (at least in mice) of the IgG1:IgG2a ratio of antigen specific antibody responses.

Thus, a Th1-type adjuvant is one which stimulates isolated T-cell populations to produce high levels of Th1-type cytokines when re-stimulated with antigen in vitro, and induces antigen specific immunoglobulin responses associated with Th1-type isotype.

Adjuvants which are capable of preferential stimulation of the Th1 cell response are described in WO 94/00153 and WO 95/17209.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described (Ribi, 1986) and has the following structure:

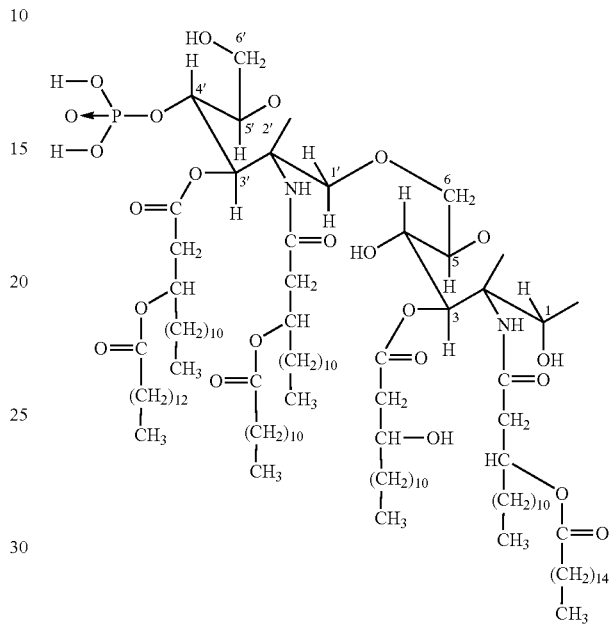

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A particular form of 3D-MPL for use in the present invention is in the form of an emulsion having a small particle size less than 0.2 um in diameter, and its method of manufacture is disclosed in WO 94/21292. Aqueous formulations comprising monophosphoryl lipid A and a surfactant have been described in WO98/43670.

The bacterial lipopolysaccharide derived adjuvants to be used in the present invention may be purified and processed from bacterial sources, or alternatively they may be synthetic. For example, purified monophosphoryl lipid A is described in Ribi et al (Ribi, 1986), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers, 1986; Hilgers, 1987; EP 0 549 074 B1). One particular bacterial lipopolysaccharide adjuvant for use in the invention is 3D-MPL.

Accordingly, the LPS derivatives that may be used in the present invention are those immunostimulants that are similar in structure to that of LPS or MPL or 3D-MPL. In another alternative the LPS derivatives may be an acylated monosaccharide, which is a sub-portion to the above structure of MPL.

Saponins are also Th1 immunostimulants. Saponins are well known adjuvants (Lacaille-Dubois, 1996). Suitable saponins for use in the invention include immunologically active saponins for example, Quil A (derived from the bark of the South American tree Quillaja Saponaria Molina), and immunologically active fractions thereof, are described in U.S. Pat. No. 5,057,540 and "Saponins as vaccine adjuvants" (Kensil, 1996) and EP 0 362 279 B1. The haemolytic saponins QS21 and QS17 (HPLC purified fractions of QuilA) have been described as potent systemic adjuvants, and the method of their production is disclosed in U.S. Pat. No. 5,057, 540 and EP 0 362 279 B1. Also described in these references is the use of QS7 (a non-haemolytic fraction of Quil-A) which acts as a potent adjuvant for systemic vaccines. Use of QS21 is further described in Kensil et al. (Kensil, 1991). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

The lipopolysaccharide and saponin immunostimulants described above for use in the invention are formulated together with a liposome carrier. For example, the carrier may comprise cholesterol containing liposomes as described in WO 96/33739.

Combinations of a monophosphoryl lipid A and a saponin derivative are described in WO 94/00153; WO 95/17210; WO 96/33739; WO 98/56414; WO 99/12565; WO 99/11241, and the combination of QS21 and 3D-MPL is disclosed in WO 94/00153.

Thus, suitable adjuvant systems for use in the invention include, for example, a combination of a monophosphoryl lipid A, such as 3D-MPL, together with a saponin derivative, particularly the combination of QS21 and 3D-MPL as disclosed in WO 94/00153. The adjuvant system includes a liposome carrier, for example cholesterol-containing liposomes, for example in a composition where the QS21 is quenched in cholesterol containing liposomes (DQ) as disclosed in WO 96/33739.

Thus the saponin such as QS21 may also be present in or associated with the membranes of the liposomes, as described in WO 96/33739. The 3D-MPL or other lipid A derivative may be present either entrapped in the membrane of the liposomes, or outside the liposomes, or both. One particular adjuvant for use in the invention comprises the two immunostimulants QS21 and 3D-MPL, in a formulation with cholesterol-containing liposomes, in which the 3D-MPL is entrapped within the liposomes and the QS21 is associated with the liposomes.

The amount of the protein of the present invention present in each vaccine dose is selected as an amount which induces an immunoprotective response without significant, adverse side effects in typical vaccines. Such amount will vary depending upon which specific immunogen is employed and which specific adjuvant. Generally, it is expected that each dose will comprise 1-1000 ug of protein, for example 1-200 ug, for example 10-100 ug. An optimal amount for a particular vaccine can be ascertained by standard studies involving observation of antibody titres and other responses in subjects.

A suitable vaccination schedule for use with the invention is a primary course prior to travel to a malaria endemic region which may be completed for example at least 2-4 weeks prior arrival in the region. This primary course may involve between 1 and 3 doses, for example 2 or 3 doses, administered with an interval of at least 7 days, or between 1 and 4 weeks or for example a month between doses. A primary vaccination course may be followed by repeated boosts every six months for as long as a risk of infection exists. Periodic booster vaccinations may then be appropriate prior to repeat travel to endemic regions. Suitable amounts of RTS,S protein per dose are as given herein above.

The vaccines of the invention may be administered by any of a variety of routes such as oral, topical, subcutaneous, mucosal (typically intravaginal), intraveneous, intramuscular, intranasal, sublingual, intradermal and via suppository.

The invention may be further used in a heterologous prime-boost regimen.

Instead of or in addition to repeat doses of the RTS,S or other polypeptide containing composition, a different form of the vaccine may be administered in a heterologous "prime-boost" vaccination regime. The priming composition and the boosting composition will have at least one antigen in common, although it is not necessarily an identical form of the antigen; it may be a different form of the same antigen.

Prime-boost immunisations according to the invention may be performed with a combination of protein and polynucleotide, particularly DNA-based formulations. Such a strategy is considered to be effective in inducing broad immune responses. Adjuvanted protein vaccines induce mainly antibodies and T helper immune responses, while delivery of DNA as a plasmid or a live vector induces strong cytotoxic T lymphocyte (CTL) responses. Thus, the combination of protein and DNA vaccination will provide for a wide variety of immune responses.

Thus the invention further provides the use of a *Plasmodium* antigen or an immunogenic fragment or derivative thereof and an adjuvant comprising a lipid A derivative and a saponin in a liposome formulation, as described herein, together with a polynucleotide encoding the *Plasmodium* antigen or an immunogenic fragment or derivative thereof, in the manufacture of a pharmaceutical kit for immunising travelers to endemic regions against productive malaria infection.

The invention also provides for a kit comprising a *Plasmodium* antigen or an immunogenic fragment or derivative thereof provided in lyophilised form, an adjuvant comprising a lipid A derivative and a saponin in a liposome formulation, and instructions specifying that the antigen, adjuvant, and optionally a further carrier, are to be mixed prior to administration to a traveler to an endemic region, thereby protecting said traveler against productive malaria infection.

Thus where RTS,S or another polypeptide based on CS protein is used as the polypeptide component of a prime-boost regimen, the polynucleotide component will encode CS protein or an immunogenic fragment or derivative thereof.

The DNA may be delivered as naked DNA such as plasmid DNA, or in the form of a recombinant live vector. Live vectors for use in the invention may be replication defective. Examples of live vectors which may be used are poxvirus vectors including modified poxvirus vectors, for example Modified Virus Ankara (MVA), alphavirus vectors for example Venezuelian Equine Encephalitis virus vectors, or adenovirus vectors for example a non-human adenovirus vector such as a chimpanzee adenovirus vector, or any other suitable live vector.

A suitable adenovirus for use as a live vector in a prime boost vaccine according to the invention is a low sero-prevalent human adenovirus such as Ad5 or Ad35 or a non-human originating adenovirus such as a non-human primate adenovirus such as a simian adenovirus. The vectors may be replication defective. Typically these viruses contain an E1 deletion and can be grown on cell lines that are transformed with an E1 gene. Suitable simian adenoviruses are viruses isolated from chimpanzee. In particular C68 (also known as Pan 9) (See U.S. Pat. No. 6,083,716) and Pan 5, 6 and Pan 7 (WO 03/046124) may be used in the present invention. These vectors can be manipulated to insert a heterologous polynucleotide according to the invention such that the polypeptides according to the invention may be expressed. The use, formulation and manufacture of such recombinant adenoviral vectors is described in detail in WO 03/046142.

Protein antigens may be injected once or several times followed by one or more DNA administrations, or DNA may be used first for one or more administrations followed by one or more protein immunisations. It may be beneficial to administer DNA first, followed by protein.

Thus a particular example of prime-boost immunisation according to the invention involves priming with a single dose of a polynucleotide in the form of a recombinant live vector such as any of those described above, followed by boosting with one or more doses, for example 2 or 3 doses, of the adjuvanted protein such as RTS,S with an adjuvant described herein. The polynucleotide encodes the same protein (e.g. CS protein) or an immunogenic fragment or derivative thereof.

Thus the invention further provides a pharmaceutical kit comprising
   a) a *Plasmodium* antigen or an immunogenic fragment or derivative thereof and an adjuvant comprising a lipid A derivative and a saponin in a liposome formulation, and
   b) a polynucleotide encoding the *Plasmodium* antigen or an immunogenic fragment or derivative thereof;
wherein a) and b) are for use sequentially in any order, but particularly wherein b) is used as the prime and a) is used as the boost. The invention also provides for instructions with said kit, specifying that, in respect of a), the antigen, adjuvant, and optionally a further carrier, are to be mixed prior to administration to a traveler to an endemic region.

The composition a) may be any polypeptide composition as described herein, in a suitable adjuvant as described herein. For example a) may be a composition comprising RTS,S and an adjuvant comprising QS21 and 3D-MPL in a liposome formulation, and b) may be a live vector as described herein such as an adenovirus vector e.g. a chimpanzee adenovirus vector, encoding CS protein or an immunogenic fragment or derivative thereof.

Both the priming composition and the boosting composition may be delivered in more than one dose. Furthermore the initial priming and boosting doses may be followed up with further doses which may be alternated to result in e.g. a DNA prime/protein boost/further DNA dose/further protein dose.

Appropriate pharmaceutically acceptable diluents or excipients for use in the invention are well known in the art and include for example water or buffers. Vaccine preparation is generally described (Powell, 1995; Voller, 1978). Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

In another aspect the invention provides a method for determining whether an individual is protected against malaria following administration of a malaria antigen composition, in particular a pre-erythrocytic malaria antigen composition, to the individual, which method comprises measuring the level of CD4 T cells raised in the individual specific for the malaria antigen. Also there is provided a method for determining whether an individual is protected against malaria following administration of a malaria antigen composition, in particular a pre-erythrocytic malaria antigen composition, to the individual, which method comprises measuring the concentration of antibodies raised in the individual specific for the malaria antigen.

In a further aspect the invention provides a method for assessing the efficacy of a candidate vaccine, particularly a pre-erythrocytic candidate vaccine, in the prevention of malaria, which method comprises measuring the level of CD4 cells raised in an individual against the candidate vaccine. Also there is provided a method for assessing the efficacy of a candidate vaccine, particularly a pre-erythrocytic candidate vaccine, in the prevention of malaria, which method comprises measuring the concentration of specific antibodies raised in an individual against the candidate vaccine. In a more specific embodiment this vaccine comprises a *Plasmodium* antigen or an immunogenic fragment or derivative thereof and an adjuvant comprising a lipid A derivative and a saponin in a liposome formulation

EXAMPLES

Example 1

Vaccination Using RTS,S and Adjuvant B and Experimental Malaria Challenge

The Vaccines

RTS,S: RTS is a 51 kDa hybrid polypeptide chain of 424 amino acids (a.a.), consisting of 189 amino acids derived from a sporozoite surface antigen (the CS protein central tandem repeat and carboxyl-terminal regions, 189 amino acids in total) of the malaria parasite *P. falciparum* strain NF54 (the CSP antigen, a.a. 207 to 395), fused to the amino terminal end of the hepatitis B virus S protein. S is a 24 kDa polypeptide (226 amino acids long) corresponding to the surface antigen of hepatitis B virus (HBsAg), and is the antigen used in the GSK Biologicals Engerix-B® vaccine.

The two proteins are produced intracellularly in yeast (*S. cerevisiae*) and spontaneously assemble into mixed polymeric particulate structures that are each estimated to contain approximately 100 polypeptides.

The preparation of RTS,S is described in WO 93/10152.

A full dose of RTS,S/AS02A (GlaxoSmithKline Biologicals, Rixensart, Belgium) contains 50 ug of lyophilised RTS,S antigen reconstituted in 500 uL of AS02A adjuvant—oil in water emulsion containing the immunostimulants 3D-MPL® (GlaxoSmithKline Biologicals, Montana, USA) and QS21, 50 ug of each.

A full dose of RTS,S/Adjuvant B (GlaxoSmithKline Biologicals, Rixensart, Belgium) contains 50 ug of lyophilised RTS,S antigen reconstituted in 500 uL of adjuvant B containing the immunostimulants 3D-MPL® and QS21 (50 ug of each) in a formulation with cholesterol-containing liposomes. The liposomes can be prepared from a mixture of de-oleic phosphatidylcholine (DOPC), cholesterol and 3D-MPL in organic solvent, wherein the mixture is dried down. An aqueous solution is then added to suspend the lipid. The suspension is microfluidised until the liposome size is reduced to be sterile filterable through a 0.2 um filter. Typically the cholesterol:phosphatidylcholine ratio is 1:4 (w/w), and the aqueous solution is added to give a final cholesterol concentration of 5 to 50 mg/ml. QS21 is added to the cholesterol-containing liposomes.

Methodology

This clinical trial has evaluated the safety, reactogenicity, immunogenicity and preliminary efficacy of a malaria vaccine containing the antigen RTS,S adjuvanted with either AS02A or adjuvant B.

103 subjects were recruited into two cohorts and were randomized to receive 3 doses of either vaccine according to a 0, 1, 2 month vaccination schedule. Because of the large numbers of subjects involved, the cohorts were recruited and challenged sequentially.

For each cohort, volunteers were requested to undergo a standardised primary malaria challenge (Chulay, 1986) two to four weeks following third dose. The primary challenge involved allowing five *P. falciparum* sporozoite infected *Anophelese stevensi* mosquitos to feed on each challenge volunteer for a period of five minutes. For each cohort, twelve unvaccinated control volunteers were also challenged.

Approximately six months after the primary challenge, volunteers who were protected at the primary challenge were asked to undergo a repeat challenge. No additional doses of vaccine were administered between challenges. The repeat challenge was carried out as for the primary challenge. For each cohort, six unvaccinated control volunteers were also challenged.

After each challenge subjects were followed daily for a period of at least 30 days to assess whether they had become infected with malaria. The principle method of detecting infection was an evaluation of a Giesma-stained peripheral blood smear to detect asexual stage parasites by light microscopy. This indicates that a subject has undergone a productive infection, with parasites having been released from the liver and progressed to erythrocytic stage. Thus sterile protection against challenge has not been achieved. At the first sign of infection subjects were declared to be positive for malaria and received a curative dose of chloroquine. The primary efficacy readout was sterile protection, that is the subject never developed asexual stage parasitaemia. In addition the time between the challenge and the appearance of parasitaemia in those that were not fully protected was recorded.

In addition, peripheral blood mononuclear cell (PBMC) samples were collected at pre-vaccination, at 2-weeks post II and at 14-28 days post III vaccination (Day of challenge: DOC).

PBMCs samples were used to evaluate CD4 and CD8 T-cell responses by cytokine flow cytometry. The latter technology allows the quantification of cells specific to a given antigen. Antigen-specific CD4 and CD8 T cells were enumerated by flow cytometry following conventional immunofluorescence labeling of cellular phenotype as well as intracellular cytokines production. Briefly, peripheral blood antigen-specific CD4 and CD8 T cells can be restimulated in vitro to produce IL-2, CD40L, TNF-alpha or IFN-gamma when incubated with their corresponding antigen. Both HBs (hepatitis B surface antigen) and CSP pools of peptide were used as antigens to restimulate antigen-specific T cells. Results were expressed as a frequency of CD4 or CD8 T-cells expressing at least two different cytokines among CD40L, IL-2, TNF-alpha, or IFN-gamma within the CD4 or CD8 T cell subpopulation.

Antibody levels are determined by evaluating antibody (IgG) responses to the *P. falciparum* CS-repeat region as measured using standard ELISA methodologies with the recombinant protein R32LR as capture antigen. Briefly, the R32LR protein [corresponding to the repeated region (NANP) of the *Plasmodium falciparum* circumsporozoite protein (CSP)] is coated onto a 96-well plates. After saturation of the plates, the serum samples serial dilutions are added directly to the plates. Antibodies to R32LR present in the serum sample will bind to the pre-coated R32LR. The plates are washed. A peroxidase labeled Goat anti-Human IgG(γ) antibody is added, and it will bind to anti-CS IgG antibodies. After another washing step, the addition of a chromogen substrate solution specific for the peroxidase provides a mean of detecting anti-CS IgG bound to the pre-coated antigen. The peroxidase catalyses a color reaction. The intensity of the color formed is proportional to the titre of the anti-CS IgG antibodies contained in the serum. Anti-repeat antibody levels are determined relative to a known serum standard run on each plate, and are expressed in μg/ml.

Results
Cohort 1:

| Adjuvant | Number of volunteers vaccinated | Number of volunteers challenged (number protected) | Number of volunteers rechallenged (number protected) |
| --- | --- | --- | --- |
| Adjuvant B | 26 | 17 (10) | 5 (3) |
| AS02A | 25 | 24 (9) | 5 (1) |
| TOTAL: | 51 | 41 | 10 |

Cohort 2:

| Adjuvant | Number of volunteers vaccinated | Number of volunteers challenged (number protected) | Number of volunteers rechallenged (number protected) |
| --- | --- | --- | --- |
| Adjuvant B | Figure not available | 19 (8) | Not done |
| AS02A | Figure not available | 20 (5) | Not done |
| TOTAL: | 52 | 39 | |

Cohorts 1 & 2 Combined for Primary Challenge:

| Adjuvant | Number of volunteers vaccinated and challenged (primary challenge) | Number of volunteers protected | Number of volunteers infected | Vaccine efficacy |
| --- | --- | --- | --- | --- |
| Adjuvant B | 36 | 18 | 18 | 50% |
| AS02A | 44 | 14 | 30 | 32% |

Thus in this trial, adjuvant B was found to be more effective at protecting naïve individuals against malaria infection. 50% of individuals challenged from the adjuvant B group were protected compared to 32% of individuals challenged from the AS02A group. This represents an improvement in protection between the two adjuvants of greater than 50%.

Furthermore, in cohort 1, adjuvant B was found to be significantly more potent than AS02A to induce CD4 T-cell responses directed against antigens present in RTS,S (FIG. 1. p=0.01663). The combined data for cohorts 1 and 2 was less significant (FIG. 2. p=0.07).

Before vaccination, there were no detectable CD4/CD8 T-cell responses directed against HBs or CSP. In contrast, at 2-week post II vaccination as well as 2-week post III vaccination (DOC: day of challenge), HBs- and CSP-specific CD4 T-cells were detected in most individuals vaccinated with both formulations. At the same time points, no detectable CD8 T-cell response was observed. These observations demonstrate that the assay used for T-cell immuno-monitoring is specific and sensitive, which is a prerequisite to perform formal comparison between groups having received different vaccine formulations.

FIG. 1 shows that individuals from cohort 1 vaccinated with RTS,S/adjuvant B have a higher frequency of CSP-specific CD4 T-cells compared to those vaccinated with RTS,S/AS02A both at 2-week post II and post III vaccination (DOC). A similar conclusion can be drawn for HBs-specific CD4 T-cells producing IFN-gamma and another cytokine among IL-2, CD40L, TNF-alpha at 2-week post II vaccination (data not shown).

FIG. 2 shows the same study as FIG. 1, except that it incorporates the data from both cohorts.

In FIGS. 1 & 2, results are expressed as a frequency of CD4 T-cells expressing at least two different cytokines among CD40L, IL-2, TNF-alpha, or IFN-gamma within $10^6$ CD4 T-cells.

A similar picture can be seen in terms of anti-CSP specific antibody responses. From FIG. 5 it can be seen that the concentration of antibodies raised in response to RTS,S/Adjuvant B was significantly greater than the concentration raised in response to RTS,S/AS02A (see particularly DOC—2 weeks post III vaccination (P=0.00793), but an effect is noticeable 2 weeks post II vaccination). Results are expressed as geometric mean concentration (GMC). Pre refers to the initial time point, before any doses are administered.

M1 refers to the time point 2 weeks after the first dose.
M2 refers to the time point 2 weeks after the second dose.
DOC refers to the 'Date of Challenge', which is 2 weeks after the third dose.

Protection Against Malaria Challenge is Associated with a Significant Higher CD4 T-Cell Response and Specific Antibody Response to CSP.

Increased immunogenicity of RTS,S/adjuvant B compared to RTS,S/AS02A does not necessary imply that it will translate into a biologically relevant effect. However, individuals vaccinated with RTS,S/adjuvant B in this trial have shown increased level of protection (18 out of 36 individuals: 50%) against malaria challenge compared to those vaccinated with RTS,S/AS02A (14 out of 44 individuals: 32%). A possible link between amplitude of CD4 T-cell response and protection to malaria has been therefore found.

If the above hypothesis is true, protected individuals should have a higher CD4 T-cell response than individuals vaccinated with RTS,S/AS02A or even RTS,S/adjuvant B. FIGS. 3 and 4, for the 1$^{st}$ cohort and the combined cohorts respectively (with both adjuvant groups pooled), clearly confirm the above hypothesis and support the idea that CSP-specific CD4 T-cells play a significant role in protection. Consistently, statistical analysis made on samples collected at 2-week post II as well as 2-week post III vaccination demonstrate that the difference in frequency between protected and non-protected individuals is statistically significant.

In FIGS. 3 and 4 results are expressed as a frequency of CD4 T-cells expressing at least two different cytokines among CD40L, IL-2, TNF-alpha, or IFN-gamma within $10^6$ CD4 T-cells. Immunogenicity analysis also indicates that, in contrast to CSP-specific CD4 T-cells, HBs-specific CD4 T-cells are not associated with protection against malaria at 2-week post II as well as 2-week post III vaccination (p=0.14 and p=0.053, receptively). This further consolidates the relevance of the above results and strongly suggests that protection is specifically linked with the presence of CD4 T-cells capable of recognizing CSP but not HBs peptides.

Finally, since there is no detectable CD8 T-cell response, it can also be concluded that, most likely, malaria pre-erythrocytic stage protection conferred by RTS,S adjuvanted with adjuvant B or AS02A is not likely due to induction of CSP-specific CD8 T-cells following vaccination.

A similar picture is observed from monitoring anti-CSP antibody responses. FIG. 6 shows antibody concentrations in protected and unprotected individuals (results relate to both cohorts with both adjuvant groups pooled). It is clear that those individuals who are protected show a significantly higher antibody concentration than those who are not protected (P<0.0001).

DISCUSSION

The above results clearly demonstrate that an association between CSP-specific CD4 T-cell and antibody responses on the one hand and protective status on the other hand against malaria challenge exists. The mechanism by which CSP-specific CD4 T-cells or antibodies would exert an anti-parasitic effect is not known. However, analysis also clearly identified a minority of individuals having a high CD4 T-cell or high antibody response that are not protected. This means that strong CD4 T-cell response or high antibody response to CSP do not alone predict protection against malaria challenge.

Different technologies have been developed to monitor T-cell responses such as lymphoproloferation, cytokine secretion, tetramer staining, elipsot or cytokine flow cytometry. The latter has been recently selected as the lead technology on the basis of excellent repeatability/reproducibility data as well as relevant marker detection (CD4, CD8, CD40L, IL-2, TNF, IFNg). A specific analytical methodology has also been identified, which resolves the high background issue often seen with cytokine flow cytometry approaches. The present report demonstrates the feasibility of using cytokine flow cytometry for robust monitoring of T-cell responses in a human clinical trial. Furthermore, it also demonstrates that it is possible to identify a marker of protection that is not directly linked to humoral immunity.

Although adjuvant B has been demonstrated to be significantly more potent than AS02A formulation to induce CSP-specific CD4 T-cells and antibodies, the difference in terms of frequency of CD4 T-cells and antibody concentrations is relatively modest and one could have concluded that it might not be relevant biologically. Data obtained in this clinical trial allow formal assessment of the biological relevance of such differences using protection against malaria data as a biologically relevant marker. Analysis clearly indicates that modest but significant differences between adjuvant in terms of T-cell frequencies and antibody concentrations translate into significantly higher degree of protection against malaria challenge.

REFERENCES

Alonso P et al. (2004) *Efficacy of the RTS,S/AS02A vaccine against Plasmodium falciparum infection and disease in young African children: randomised controlled trial*. Lancet October; 364:1411-1420.

Alonso et al. (2005) *Duration of protection with RTS,S/AS02A malaria vaccine in prevention of Plasmodium falciparum disease in Mozambican children: single-blind extended follow-up of a randomised controlled trial*. Lancet. December 10; 366(9502):2012-8.

Ballou W R, Arevalo-Herrera M, Carucci D, Richie T L, Corradin G, Diggs C, et al. (2004) *Update on the clinical development of candidate malaria vaccines*. Am J Trop Med Hyg; 71(2_suppl):239-247.

Bojang K A, Milligan P J M, Pinder M, Vigneron L, Alloueche A, Kester K E, et al. (2001) *Efficacy of RTS,S/AS02 malaria vaccine against Plasmodium falciparum infection in semi-immune adult men in The Gambia: a randomised trial*. The Lancet; 358(9297):1927-1934.

Bojang K A, Olodude F, Pinder M, Ofori-Anyinam O, Vigneron L, Fitzpatrick S, Njie F, Kassanga A, Leach A, Milman J, Rabinovich R, McAdam K P W J, Kester K E, Heppner D G, Cohen J D, Tornieporth N, and Milligan P J M. (2005) *Safety and immunogenicity of RTS,S/AS02A candidate malaria vaccine in Gambian children*. Vaccine 23(32): 4148-57.

Breman J G, Alilio M S, Mills A. (2004) *The intolerable burden of malaria: what's new, what's needed*. Am J Trop Med Hyg; 71(2_suppl):0-i-.

Caspers et al. (1989) *The circumsporozoite protein gene from NF54, a Plasmodium falciparum isolate used in malaria vaccine trials*. Mol. Biochem. Parasitol 35, 185-190.

Chulay et al, (1986) *Malaria transmitted to humans by mosquitoes infected from cultured Plasmodium falciparum*. Am J Trop Med Hyg. January:35(1):66-8

Doherty J, Pinder M, Tornieporth N, Carton C, Vigneron L, Milligan P, et al. (1999) *A phase I safety and immunogenicity trial with the candidate malaria vaccine RTS,S/SBAS2 in semi-immune adults in The Gambia*. Am J Trop Med Hyg; 61(6):865-868.

Hay S I, Guerra C A, Tatem A J, Noor A M, Snow R W. (2004) *The global distribution and population at risk of malaria: past, present, and future*. The Lancet Infectious Diseases; 4(6):327-336.

Hilgers et al. (1986). *Synergistic effects of synthetic adjuvants on the humoral immune response*. Int. Arch. Allergy. Immunol., 79(4):392-6

Hilgers et al. (1987). *Synthetic sulpholipopolysaccharides: novel adjuvants for humoral immune responses*. Immunology, 60(1):141-6.

Hoffman S L (1996) "Malaria Vaccine Development: a multi-immune response approach" Am Soc Microbiol Press Ed Hoffman S L, Chapter 3 "Attacking the infected hepatocyte"

Kensil C R, Patel U, Lennick M, Marciani D. (1991) *Separation and characterization of saponins with adjuvant activity from Quillaja saponaria Molina cortex*. J. Immunology vol 146, 431-437

Kensil, C. R. (1996) *Saponins as vaccine adjuvants*. Crit Rev Ther Drug Carrier Syst 12 (1-2):1-55

Kester K E, McKinney D A, Tornieporth N, et al. (2001) *Efficacy of recombinant circumsporozoite protein vaccine regimens against experimental Plasmodium falciparum malaria*. J. Infect. Dis.; 183(4):640-7.

Lacaille-Dubois, M and Wagner H., (1996) *A review of the biological and pharmacological activities of saponins*. Phytomedicine vol 2 pp 363-386

Lalvani A, Moris P, Voss G, et al. (1999) *Potent induction of focused Th1-type cellular and humoral immune responses by RTS,S/SBAS2, a recombinant Plasmodium falciparum malaria vaccine*. J. Infect. Dis.; 180(5):1656-64.

Macete E, Aponte J J, Guinovart C, Sacarlal J, Mandomando I, Espasa M, et al. *Safety, reactogenicity and immunogenicty of the RTS,S/AS02A candidate malaria vaccine in children aged 1 to 4 years in Mozambique*. Vaccine submitted.

Mosmann, T. R. and Coffman, R. L. (1989) *Th1 and Th2 cells: different patterns of lymphokine secretion lead to different functional properties*. Annual Review of Immunology, 7, p 145-173

Musti A. M. et al., (1983) *Transcriptional mapping of two yeast genes coding for glyceraldehyde 3-phosphate dehydrogenase isolated by sequence homology with the chicken gene*. Gene 1983, 25 133-143.

Powell and Newman (Editors) (1995) *Vaccine Design—the subunit and adjuvant approach*. Pharmaceutical Biotechnology, Vol. 61, Plenum Press New York.

Ribi et al, (1986) *Modulation of humoral and cell-mediated immune responses by a structurally established nontoxic lipid A*. Immunobiology and Immunopharmacology of bacterial endotoxins. Plenum Publ. Corp., NY, p 407-420

Stoute J, Slaoui M, Heppner D, Momin P, Kester K, Desmons P, et al. (1997) *A preliminary evaluation of a recombinant circumsporozoite protein vaccine against Plasmodium falciparum malaria. RTS,S Malaria Vaccine Evaluation Group*. N Engl J Med; 336(2):86-91.

Stoute, J A, Kester K E, Krzych U, Wellde B T, Hall T, White K, Glenn G, Ockenhouse C F, Garçon N, Schwenk R, Lanar D E, Momin P, Golenda C, Slaoui M, Wortmann G, Cohen J, Ballou W R. (1998) *Long Term Efficacy and Immune Responses Following Immunization with the RTS,S Malaria Vaccine*. J Infect Dis 178:1139-44.

Sun P, Schwenk R, White K, Stoute J A, Cohen J, Ballou W R, Voss G, Kester K E, Heppner D G, Krzych U. (2003) *Protective immunity induced with malaria vaccine, RTS,S, is linked to Plasmodium falciparum circumsporozoite protein-specific CD4(+) and CD8(+) T cells producing IFN-gamma*. J Immunol. December 15; 171(12): 6961-7.

Valenzuela P, Gray P, Quiroga M, Zaldivar J, Goodman H, Rutter W. (1979) *Nucleotide sequence of the gene coding for the major protein of hepatitis B virus surface antigen*. Nature 280, 815-819.

Voller et al. (Editor) (1978) *New Trends and Developments in Vaccines*. University Park Press, Baltimore, Md., U.S.A.

The invention claimed is:

1. A method of protecting malaria-naïve human subjects against productive malaria infection due to *Plasmodium falciparum* comprising:
   (i) selecting malaria-naïve human subjects and
   (ii) administering to said malaria-naïve human subjects a formulation comprising:
      (a) an immunogenic amount of the RTS,S malaria vaccine comprising the RTS hybrid protein and the S protein of hepatitis B virus (HBsAg) in the form of mixed particles, wherein the RTS hybrid protein comprises substantially all the C-terminal portion of the circumsporozoite (CS) protein of *Plasmodium falciparum* and
      (b) adjuvant B comprising 3D-MPL and QS21, the QS21 quenched in cholesterol-containing liposomes, thereby protecting the malaria-naïve human subjects against the productive malaria infection due to *Plasmodium falciparum*.

2. The method of claim 1, wherein the RTS hybrid protein comprises a sequence of amino acids 207-395 of the *Plasmodium falciparum* CS protein from clone 3D7 from the NF54 strain of *Plasmodium falciparum*.

3. The method of claim 1, wherein the amount of the RTS,S per dose is 25 micrograms or 50 micrograms.

4. The method of claim 1, wherein a CD4 T-cell response against the CS protein is induced in the malaria-naïve human subjects.

* * * * *